(12) United States Patent
Wu et al.

(10) Patent No.: US 12,297,267 B2
(45) Date of Patent: May 13, 2025

(54) HUMANIZED ANTI-CD19 ANTIBODY AND USE THEREOF WITH CHIMERIC ANTIGEN RECEPTOR

(71) Applicant: Innovative Cellular Therapeutics Holdings, Ltd., George Town (KY)

(72) Inventors: Zhao Wu, Shanghai (CN); Zhigang Liu, Shanghai (CN); Lei Xiao, Rockville, MD (US); Chengfei Pu, Shanghai (CN); Zhiyuan Cao, Shanghai (CN)

(73) Assignee: Innovative Cellular Therapeutics Holdings, Ltd., George Town (KY)

( * ) Notice: Subject to any disclaimer, the term of this patent is extended or adjusted under 35 U.S.C. 154(b) by 419 days.

(21) Appl. No.: 17/725,623

(22) Filed: Apr. 21, 2022

(65) Prior Publication Data

US 2022/0249638 A1 Aug. 11, 2022

Related U.S. Application Data

(60) Division of application No. 16/600,064, filed on Oct. 11, 2019, now Pat. No. 11,364,289, which is a division of application No. 15/876,538, filed on Jan. 22, 2018, now Pat. No. 10,493,139, which is a continuation-in-part of application No. PCT/CN2017/070208, filed on Jan. 5, 2017, and a continuation-in-part of application No. PCT/CN2015/084991, filed on Jul. 24, 2015.

(51) Int. Cl.
  *C07K 16/00* (2006.01)
  *A61K 39/00* (2006.01)
  *A61P 35/00* (2006.01)
  *C07K 16/28* (2006.01)

(52) U.S. Cl.
  CPC ...... *C07K 16/2803* (2013.01); *A61K 39/4611* (2023.05); *A61K 39/4631* (2023.05); *A61K 39/464412* (2023.05); *A61P 35/00* (2018.01); *A61K 2239/48* (2023.05); *C07K 2317/24* (2013.01); *C07K 2317/55* (2013.01); *C07K 2317/56* (2013.01); *C07K 2317/622* (2013.01); *C07K 2317/73* (2013.01); *C07K 2319/02* (2013.01); *C07K 2319/03* (2013.01); *C07K 2319/43* (2013.01)

(58) Field of Classification Search
  CPC ............ C07K 16/2803; C07K 2317/56; C07K 2317/622; A61K 39/4611; A61K 39/4631; A61K 39/464412; A61P 35/00
  See application file for complete search history.

(56) References Cited

U.S. PATENT DOCUMENTS

| 8,906,682 B2 | 12/2014 | June et al. |
| 2010/0215651 A1 | 8/2010 | Blein |
| 2018/0153977 A1 | 6/2018 | Wu et al. |
| 2020/0030424 A1 | 1/2020 | Wu et al. |

FOREIGN PATENT DOCUMENTS

| WO | WO2005012493 A2 | 2/2005 |
| WO | WO2007002223 A2 | 1/2007 |
| WO | WO2010095031 A2 | 8/2010 |
| WO | WO2010102276 A2 | 9/2010 |
| WO | WO2012010562 A1 | 1/2012 |
| WO | WO2013138244 A2 | 9/2013 |
| WO | WO2014153270 A1 | 9/2014 |
| WO | WO2016033570 A1 | 3/2016 |
| WO | WO2016187349 A1 | 11/2016 |
| WO | WO2017015783 A1 | 2/2017 |

OTHER PUBLICATIONS

Extended European Search Report mailed Sep. 21, 2022 for European Patent Application No. 22152822.7, 10 pages.
European Office Action mailed Jun. 20, 2022 for European Patent Application No. 22152822.7, a foreign counterpart to U.S. Pat. No. 10,493,139, 10 pages.
European Office Action mailed Mar. 4, 2021 for European Patent Application No. 17889643.7, a foreign counterpart of U.S. Pat. No. 10,493,139, 3 pages.
European Search Report dated Jul. 20, 2020 in European Application No. 17889643.7, a foreign corresponding application of U.S. Appl. No. 15/876,538, 5 pages.
International Search Report and Written Opinion in International Application No. PCT/CN2017/084991, mailed Oct. 12, 2017, 11 pages.
International Search Report and Written Opinion in International Application No. PCT/CN2015/084991, mailed Apr. 28, 2016, 13 pages.
Kugler M, et al., "Stabilization and humanization of a single-chain Fv antibody fragment 1-36 specific for human lymphocyte antigen CD19 by designed point mutations and CDR-grafting onto a human framework," Mar. 31, 2009, Protein Eng Des Sel, vol. 22, No. 3.

*Primary Examiner* — Lei Yao
(74) *Attorney, Agent, or Firm* — Lee & Hayes, P.C.

(57) ABSTRACT

Embodiments herein relate to humanized CD19 antibodies and disease treatment using the antibodies. For example, a subject having a CD19 positive tumor may be administered a therapeutically effective amount of the humanized antibody.

16 Claims, 13 Drawing Sheets

Specification includes a Sequence Listing.

L2D8

DIQMTQSPSSLSASVGDRVTITCRASQSVGSFLAWYQQKPGKAPKLLIYGASSRESGVPSRFSGSGSGTDFTLTI
SSLQPEDFATYYCQQTYHNPETFGQGTKVEIK

L2D12

SYELTQPPSVSVAPGQTARITCGGNDLRAQYVHWYQQKPGQAPVLVMVYDDSKRPSGIPERFSGSNSGNTATL
TISGTQAEDEADYYCQSWDRTSEPKVFGGGTKLTVL

L5F3

SYELTQPPSVSVAPGQTARITCGGNNLGDNSARWYQQKPGQAPVLVIYGNSNRPSGIPERFSGSNSGNTATL
TISGTQAEDEADYYCQVTDTRSTSVVFGGGTKLTVL

FIG. 2

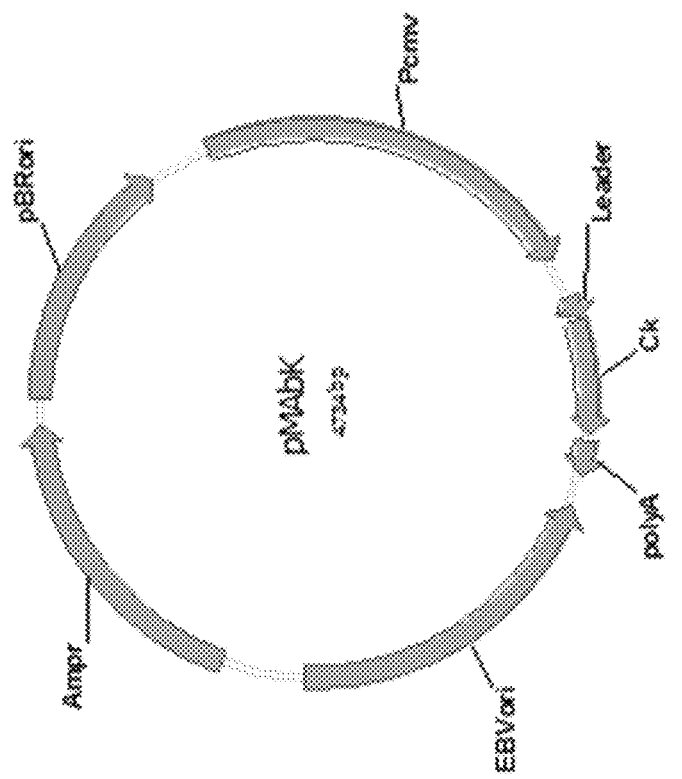
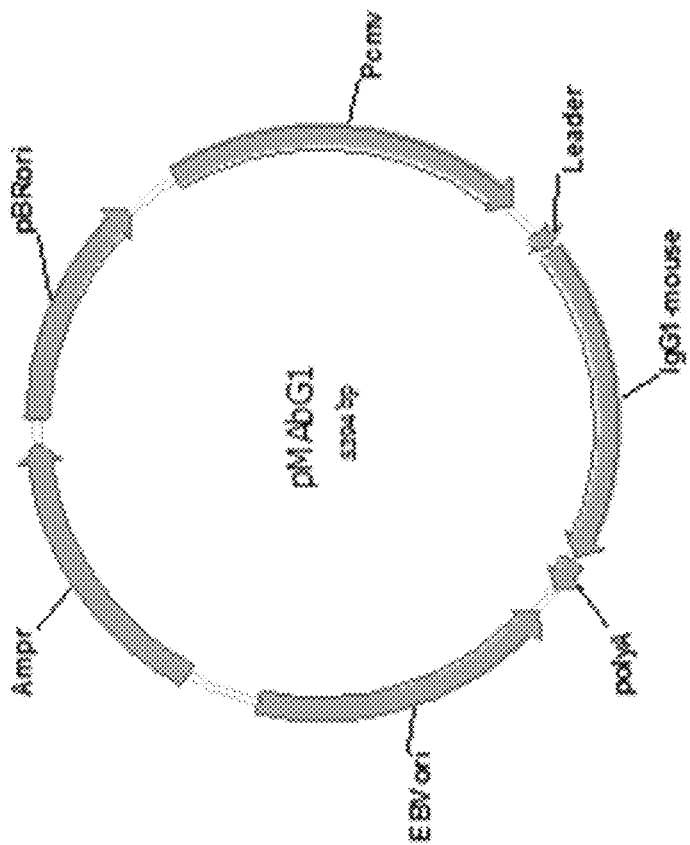
FIG. 8

SEQUENCE LISTING

<160> NUMBER OF SEQ ID NOS: 45

<210> SEQ ID NO 1
<211> LENGTH: 120
<212> TYPE: PRT
<213> ORGANISM: Mus musculus

<400> SEQUENCE: 1

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 2
<211> LENGTH: 107
<212> TYPE: PRT
<213> ORGANISM: Mus musculus

<400> SEQUENCE: 2

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 3
<211> LENGTH: 120
<212> TYPE: PRT
<213> ORGANISM: Artificial Sequence
<220> FEATURE:
<223> OTHER INFORMATION: Synthesized

<400> SEQUENCE: 3

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Arg Lys Gly Leu Glu Trp Leu
            35                  40                  45

Gly Val Ile Trp Gly Ser Glu Thr Thr Tyr Tyr Asn Ser Ala Leu Lys
50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 4
<211> LENGTH: 107
<212> TYPE: PRT
<213> ORGANISM: Artificial Sequence
<220> FEATURE:
<223> OTHER INFORMATION: Synthesized

<400> SEQUENCE: 4

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105

<210> SEQ ID NO 5
<211> LENGTH: 360
<212> TYPE: DNA
<213> ORGANISM: Artificial Sequence
<220> FEATURE:
<223> OTHER INFORMATION: Synthesized

<400> SEQUENCE: 5
gaggtgaaac tgcaggagtc aggacctggc ctggtggcgc catcacagag cctgtccgtc      60
acatgcactg tctcaggggt ctcattacct gactatggtg taagctggat tcgccagcct     120
ccacgcaagg gtctggagtg gctgggagta atctggggta gtgaaaccac atactataat     180
tcagctctca aatcccgcct gaccatcatc aaggacaact ccaagagcca gttttcttta     240
aaaatgaaca gtctgcaaac tgatgacaca gccatttact actgtgccaa acattattac     300
tacggtggta gctatgctat ggactactgg ggtcaaggaa cctcagtcac cgtctcctca     360

<210> SEQ ID NO 6
<211> LENGTH: 321
<212> TYPE: DNA
<213> ORGANISM: Artificial Sequence
<220> FEATURE:
<223> OTHER INFORMATION: Synthesized

<400> SEQUENCE: 6

```
gacatccaga tgacacagac tacatcctcc ctgtctgcct ctctgggaga ccgcgtcacc    60
atcagttgcc gtgcaagtca ggacattagt aaatacttaa attggtatca gcagaaacca   120
gatggaactg ttaaactcct gatctaccat acatcacgct tacactcagg agtcccatca   180
cggttcagtg gcagtgggtc tggaacagat tattctctca ccattagcaa cctggagcaa   240
gaagatattg ccacttactt ttgccaacag ggtaatacgc ttccgtacac gttcggaggg   300
gggactaagt tggaaatcaa a                                             321
```

<210> SEQ ID NO 7
<211> LENGTH: 10
<212> TYPE: PRT
<213> ORGANISM: Artificial Sequence
<220> FEATURE:
<223> OTHER INFORMATION: Synthesized

<400> SEQUENCE: 7

```
Gly Val Ser Leu Pro Asp Tyr Gly Val Ser
1               5                   10
```

<210> SEQ ID NO 8
<211> LENGTH: 16
<212> TYPE: PRT
<213> ORGANISM: Artificial Sequence
<220> FEATURE:
<223> OTHER INFORMATION: Synthesized

<400> SEQUENCE: 8

```
Val Ile Trp Gly Ser Glu Thr Thr Tyr Tyr Asn Ser Ala Leu Lys Ser
1               5                   10                  15
```

<210> SEQ ID NO 9
<211> LENGTH: 13
<212> TYPE: PRT
<213> ORGANISM: Artificial Sequence
<220> FEATURE:
<223> OTHER INFORMATION: Synthesized

<400> SEQUENCE: 9

```
Lys His Tyr Tyr Tyr Gly Gly Ser Tyr Ala Met Asp Tyr
1               5                   10
```

<210> SEQ ID NO 10
<211> LENGTH: 25
<212> TYPE: PRT
<213> ORGANISM: Artificial Sequence
<220> FEATURE:
<223> OTHER INFORMATION: Synthesized

<400> SEQUENCE: 10

```
Glu Val Lys Leu Gln Glu Ser Gly Pro Gly Leu Val Ala Pro Ser Gln
1               5                   10                  15

Ser Leu Ser Val Thr Cys Thr Val Ser
            20                  25
```

<210> SEQ ID NO 11
<211> LENGTH: 14
<212> TYPE: PRT
<213> ORGANISM: Artificial Sequence
<220> FEATURE:
<223> OTHER INFORMATION: Synthesized

<400> SEQUENCE: 11

```
Trp Ile Arg Gln Pro Pro Arg Lys Gly Leu Glu Trp Leu Gly
1               5                   10
```

<210> SEQ ID NO 12
<211> LENGTH: 31
<212> TYPE: PRT
<213> ORGANISM: Artificial Sequence
<220> FEATURE:
<223> OTHER INFORMATION: Synthesized

<400> SEQUENCE: 12

```
Arg Leu Thr Ile Ile Lys Asp Asn Ser Lys Ser Gln Val Phe Leu Lys
1               5                   10                  15

Met Asn Ser Leu Gln Thr Asp Asp Thr Ala Ile Tyr Tyr Cys Ala
            20                  25                  30
```

<210> SEQ ID NO 13
<211> LENGTH: 11
<212> TYPE: PRT
<213> ORGANISM: Artificial Sequence
<220> FEATURE:
<223> OTHER INFORMATION: Synthesized

<400> SEQUENCE: 13

```
Trp Gly Gln Gly Thr Ser Val Thr Val Ser Ser
1               5                   10
```

<210> SEQ ID NO 14
<211> LENGTH: 8
<212> TYPE: PRT
<213> ORGANISM: Artificial Sequence
<220> FEATURE:
<223> OTHER INFORMATION: Synthesized

<400> SEQUENCE: 14

```
Gly Val Ser Leu Pro Asp Tyr Gly
1               5
```

<210> SEQ ID NO 15
<211> LENGTH: 7
<212> TYPE: PRT
<213> ORGANISM: Artificial Sequence
<220> FEATURE:
<223> OTHER INFORMATION: Synthesized

<400> SEQUENCE: 15

```
Ile Trp Gly Ser Glu Thr Thr
1               5
```

<210> SEQ ID NO 16
<211> LENGTH: 13
<212> TYPE: PRT
<213> ORGANISM: Artificial Sequence
<220> FEATURE:
<223> OTHER INFORMATION: Synthesized

<400> SEQUENCE: 16

```
Lys His Tyr Tyr Tyr Gly Gly Ser Tyr Ala Met Asp Tyr
1               5                   10
```

<210> SEQ ID NO 17
<211> LENGTH: 25
<212> TYPE: PRT
<213> ORGANISM: Artificial Sequence
<220> FEATURE:
<223> OTHER INFORMATION: Synthesized

```
<400> SEQUENCE: 17

Glu Val Lys Leu Gln Glu Ser Gly Pro Gly Leu Val Ala Pro Ser Gln
1               5                   10                  15

Ser Leu Ser Val Thr Cys Thr Val Ser
            20                  25

<210> SEQ ID NO 18
<211> LENGTH: 17
<212> TYPE: PRT
<213> ORGANISM: Artificial Sequence
<220> FEATURE:
<223> OTHER INFORMATION: Synthesized

<400> SEQUENCE: 18

Val Ser Trp Ile Arg Gln Pro Pro Arg Lys Gly Leu Glu Trp Leu Gly
1               5                   10                  15

Val

<210> SEQ ID NO 19
<211> LENGTH: 39
<212> TYPE: PRT
<213> ORGANISM: Artificial Sequence
<220> FEATURE:
<223> OTHER INFORMATION: Synthesized

<400> SEQUENCE: 19

Tyr Tyr Asn Ser Ala Leu Lys Ser Arg Leu Thr Ile Ile Lys Asp Asn
1               5                   10                  15

Ser Lys Ser Gln Val Phe Leu Lys Met Asn Ser Leu Gln Thr Asp Asp
            20                  25                  30

Thr Ala Ile Tyr Tyr Cys Ala
        35

<210> SEQ ID NO 20
<211> LENGTH: 11
<212> TYPE: PRT
<213> ORGANISM: Artificial Sequence
<220> FEATURE:
<223> OTHER INFORMATION: Synthesized

<400> SEQUENCE: 20

Trp Gly Gln Gly Thr Ser Val Thr Val Ser Ser
1               5                   10

<210> SEQ ID NO 21
<211> LENGTH: 98
<212> TYPE: PRT
<213> ORGANISM: Artificial Sequence
<220> FEATURE:
<223> OTHER INFORMATION: Synthesized

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

Leu Gln Met Asn Ser Leu Arg Ala Glu Asp Thr Ala Val Tyr Tyr Cys
                85                  90                  95

Ala Arg

<210> SEQ ID NO 22
<211> LENGTH: 96
<212> TYPE: PRT
<213> ORGANISM: Artificial Sequence
<220> FEATURE:
<223> OTHER INFORMATION: Synthesized

<400> SEQUENCE: 22

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Arg Ile Tyr Tyr Ser Gly Ser Thr Tyr Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

<210> SEQ ID NO 23
<211> LENGTH: 20
<212> TYPE: PRT
<213> ORGANISM: Artificial Sequence
<220> FEATURE:
<223> OTHER INFORMATION: Synthesized

<400> SEQUENCE: 23

Tyr Tyr Tyr Tyr Tyr Gly Met Asp Val Trp Gly Gln Gly Thr Thr Val
1               5                   10                  15

Thr Val Ser Ser
            20

<210> SEQ ID NO 24
<211> LENGTH: 15
<212> TYPE: PRT
<213> ORGANISM: Artificial Sequence
<220> FEATURE:
<223> OTHER INFORMATION: Synthesized

<400> SEQUENCE: 24

Tyr Phe Asp Tyr Trp Gly Gln Gly Thr Leu Val Thr Val Ser Ser
1               5                   10                  15

<210> SEQ ID NO 25
<211> LENGTH: 120
<212> TYPE: PRT
<213> ORGANISM: Artificial Sequence
<220> FEATURE:
<223> OTHER INFORMATION: Synthesized

<400> SEQUENCE: 25

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

```
Gly Trp Ser Trp Ile Arg Gln Pro Pro Gly Lys Gly Leu Glu Trp Ile
            35                  40                  45

Gly Arg Ile Trp Gly Ser Glu Thr Thr Tyr Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Leu Val Thr Val Ser Ser
            115                 120

<210> SEQ ID NO 26
<211> LENGTH: 120
<212> TYPE: PRT
<213> ORGANISM: Artificial Sequence
<220> FEATURE:
<223> OTHER INFORMATION: Synthesized

<400> SEQUENCE: 26

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
            35                  40                  45

Gly Val Ile Trp Gly Ser Glu Thr Thr Tyr Tyr Asn Ser Ala Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Leu Val Thr Val Ser Ser
            115                 120

<210> SEQ ID NO 27
<211> LENGTH: 120
<212> TYPE: PRT
<213> ORGANISM: Artificial Sequence
<220> FEATURE:
<223> OTHER INFORMATION: Synthesized

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
            35                  40                  45

Ser Val Ile Trp Gly Ser Glu Thr Thr Tyr Tyr Asn Ser Ala Leu Lys
        50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95
```

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 28
<211> LENGTH: 360
<212> TYPE: DNA
<213> ORGANISM: Artificial Sequence
<220> FEATURE:
<223> OTHER INFORMATION: Synthesized

<400> SEQUENCE: 28
caggtgcaac tgcaggagtc gggcccagga ctggtgaagc cttcggagac cctgtccctc      60
acctgcactg tctctggggt ctcattacca gactatggtt ggagctggat tcggcagccg     120
ccggggaagg gactggagtg gattgggcgt atctggggta gtgaaaccac atactacaac     180
ccgtccctca gagtcgcgt caccatttcc gtagacacgt ccaagaacca gttctccctg      240
aagctgagct ctgtgaccgc cgcagacacg gctgtgtatt actgtgcgaa acattattac     300
tacggtggta gctatgctat ggactactgg ggccaaggaa ccctggtcac cgtctcctca     360

<210> SEQ ID NO 29
<211> LENGTH: 360
<212> TYPE: DNA
<213> ORGANISM: Artificial Sequence
<220> FEATURE:
<223> OTHER INFORMATION: Synthesized

<400> SEQUENCE: 29
caggtgcaac tgcaggagtc gggcccagga ctggtgaagc cttcggagac cctgtccctc      60
acctgcactg tctctggggt ctcattacca gactatggtg tgagctggat tcggcagccg     120
ccggggaagg gactggagtg gattggggtt atctggggta gtgaaaccac atactacaac     180
agcgccctca gagtcgcgt caccatttcc gtagacacgt ccaagaacca gttctccctg      240
aagctgagct ctgtgaccgc cgcagacacg gctgtgtatt actgtgcgaa acattattac     300
tacggtggta gctatgctat ggactactgg ggccaaggaa ccctggtcac cgtctcctca     360

<210> SEQ ID NO 30
<211> LENGTH: 360
<212> TYPE: DNA
<213> ORGANISM: Artificial Sequence
<220> FEATURE:
<223> OTHER INFORMATION: Synthesized

<400> SEQUENCE: 30
gaggtgcagc tggtggagtc tgggggaggc ttggtacagc ctggggggtc cctgagactc      60
tcctgtgcag cctctggagt gtccctgcct gattatggcg tgtcctgggt ccgccaggct     120
ccagggaagg ggctggagtg ggtttcagtg atctggggca gcgagacaac ctactacaac     180
agcgccctga agtcccgatt caccatctcc agagacaatg ccaagaactc actgtatctg     240
caaatgaaca gcctgagagc cgaggacacg gctgtgtatt actgtgcgaa gcactactac     300
tacggcggca gctacgctat ggactactgg ggccaaggaa ccctggtcac cgtctcctca     360

<210> SEQ ID NO 31
<211> LENGTH: 321
<212> TYPE: DNA
<213> ORGANISM: Artificial Sequence
<220> FEATURE:

<223> OTHER INFORMATION: Synthesized

<400> SEQUENCE: 31

```
gatatccaga tgacccagag cccgagcagc ctgagcgcga gcgtgggtga tcgcgtgacc      60
attacctgcc gcgcgagcca gagtgtcggt agcttcctgg cttggtatca gcagaaaccg     120
ggtaaagcgc cgaaactgtt aatttatggt gccagcagcc gggagtctgg cgtgccgtcg     180
cgttttagcg gctcgggttc gggcaccgat tttacccctga ccatctcgag cttgcagccg     240
gaggacttcg ccacctacta ttgccagcaa acctaccata acccagagac cttcggtcag     300
ggcaccaaag tggagatcaa a                                               321
```

<210> SEQ ID NO 32
<211> LENGTH: 324
<212> TYPE: DNA
<213> ORGANISM: Artificial Sequence
<220> FEATURE:
<223> OTHER INFORMATION: Synthesized

<400> SEQUENCE: 32

```
agctacgaac tgacccagcc gccgagcgtg tcggtggcgc cgggtcagac cgcgcgtatc      60
acctgcggcg gcaacgacct ccgtgcccag tatgtccatt ggtatcagca gaaaccgggt     120
caggcaccgg tgctggtgat gtacgacgat agtaagcgcc cgtctggcat cccggaacgc     180
tttagcggct cgaattcggg caacaccgcg accctgacca ttagcggcac ccaggcggag     240
gatgaggcgg actattactg ccagtcatgg gacaggacga gcgaacctaa ggtgtttggc     300
ggtggcacca aactgaccgt gcta                                            324
```

<210> SEQ ID NO 33
<211> LENGTH: 324
<212> TYPE: DNA
<213> ORGANISM: Artificial Sequence
<220> FEATURE:
<223> OTHER INFORMATION: Synthesized

<400> SEQUENCE: 33

```
agctacgaac tgacccagcc gccgagcgtg tcggtggcgc cgggtcagac cgcgcgtatc      60
acctgcggcg gcaacaacct tggtgacaac tctgctcgtt ggtatcagca gaaaccgggt     120
caggcaccgg tgctggtgat ttacggcaac agtaatcgcc cgtctggcat cccggaacgt     180
tttagcggct cgaattcggg caacaccgcg accctgacca ttagcggcac ccaggcggag     240
gatgaggcgg actattactg ccaggtgacg gacacaagaa gcacatctgt ggtgtttggc     300
ggtggcacca aactgaccgt gcta                                            324
```

<210> SEQ ID NO 34
<211> LENGTH: 107
<212> TYPE: PRT
<213> ORGANISM: Artificial Sequence
<220> FEATURE:
<223> OTHER INFORMATION: Synthesized

<400> SEQUENCE: 34

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Gly Ser Phe
            20                  25                  30

Leu Ala Trp Tyr Gln Gln Lys Pro Gly Lys Ala Pro Lys Leu Leu Ile
        35                  40                  45
```

```
Tyr Gly Ala Ser Ser Arg Glu Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Tyr His Asn Pro Glu
                    85                  90                  95

Thr Phe Gly Gln Gly Thr Lys Val Glu Ile Lys
                100                 105

<210> SEQ ID NO 35
<211> LENGTH: 108
<212> TYPE: PRT
<213> ORGANISM: Artificial Sequence
<220> FEATURE:
<223> OTHER INFORMATION: Synthesized

<400> SEQUENCE: 35

Ser Tyr Glu Leu Thr Gln Pro Pro Ser Val Ser Val Ala Pro Gly Gln
 1               5                  10                  15

Thr Ala Arg Ile Thr Cys Gly Gly Asn Asp Leu Arg Ala Gln Tyr Val
                20                  25                  30

His Trp Tyr Gln Gln Lys Pro Gly Gln Ala Pro Val Leu Val Met Tyr
                35                  40                  45

Asp Asp Ser Lys Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Trp Asp Arg Thr Ser Glu Pro
                    85                  90                  95

Lys Val Phe Gly Gly Gly Thr Lys Leu Thr Val Leu
                100                 105

<210> SEQ ID NO 36
<211> LENGTH: 108
<212> TYPE: PRT
<213> ORGANISM: Artificial Sequence
<220> FEATURE:
<223> OTHER INFORMATION: Synthesized

<400> SEQUENCE: 36

Ser Tyr Glu Leu Thr Gln Pro Pro Ser Val Ser Val Ala Pro Gly Gln
 1               5                  10                  15

Thr Ala Arg Ile Thr Cys Gly Gly Asn Asn Leu Gly Asp Asn Ser Ala
                20                  25                  30

Arg Trp Tyr Gln Gln Lys Pro Gly Gln Ala Pro Val Leu Val Ile Tyr
                35                  40                  45

Gly Asn Ser Asn Arg Pro Ser Gly Ile Pro Glu Arg Phe Ser Gly Ser
            50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Val Thr Asp Thr Arg Ser Thr Ser
                    85                  90                  95

Val Val Phe Gly Gly Gly Thr Lys Leu Thr Val Leu
                100                 105

<210> SEQ ID NO 37
<211> LENGTH: 107
<212> TYPE: PRT
<213> ORGANISM: Artificial Sequence
```

<220> FEATURE:
<223> OTHER INFORMATION: Synthesized

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105

<210> SEQ ID NO 38
<211> LENGTH: 321
<212> TYPE: DNA
<213> ORGANISM: Artificial Sequence
<220> FEATURE:
<223> OTHER INFORMATION: Synthesized

<400> SEQUENCE: 38
gatatccaga tgacccagag cccgagcagc ctgagcgcga gcgtgggtga tcgcgtgacc        60
attacctgca gggcaagtca ggacattagt aaatatttaa attggtatca gcagaaaccg       120
ggtaaagcgc cgaaactgtt aatttatcat acatcaagat tacactcagg cgtgccgtcg       180
cgttttagcg gctcgggttc gggcaccgat tttaccctga ccatctcgag cttgcagccg       240
gaggacttcg ccacctacta ttgccaacag ggtaatacgc ttccgtacac gttcggtcag       300
ggcaccaaag tggagatcaa a                                                 321

<210> SEQ ID NO 39
<211> LENGTH: 21
<212> TYPE: PRT
<213> ORGANISM: Artificial Sequence
<220> FEATURE:
<223> OTHER INFORMATION: synthesized

<400> SEQUENCE: 39

Met Ala Leu Pro Val Thr Ala Leu Leu Leu Pro Leu Ala Leu Leu Leu
1               5                   10                  15

His Ala Ala Arg Pro
            20

<210> SEQ ID NO 40
<211> LENGTH: 69
<212> TYPE: PRT
<213> ORGANISM: Artificial Sequence
<220> FEATURE:
<223> OTHER INFORMATION: synthesized

<400> SEQUENCE: 40

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

```
Ala Ala Gly Gly Ala Val His Thr Arg Gly Leu Asp Phe Ala Cys Asp
            35                  40                  45

Ile Tyr Ile Trp Ala Pro Leu Ala Gly Thr Cys Gly Val Leu Leu Leu
 50                  55                  60

Ser Leu Val Ile Thr
 65
```

<210> SEQ ID NO 41
<211> LENGTH: 42
<212> TYPE: PRT
<213> ORGANISM: Artificial Sequence
<220> FEATURE:
<223> OTHER INFORMATION: Synthesized

<400> SEQUENCE: 41

```
Lys Arg Gly Arg Lys Lys Leu Leu Tyr Ile Phe Lys Gln Pro Phe Met
 1               5                  10                  15

Arg Pro Val Gln Thr Thr Gln Glu Asp Gly Cys Ser Cys Arg Phe
            20                  25                  30

Pro Glu Glu Glu Glu Gly Gly Cys Glu Leu
            35                  40
```

<210> SEQ ID NO 42
<211> LENGTH: 112
<212> TYPE: PRT
<213> ORGANISM: Artificial Sequence
<220> FEATURE:
<223> OTHER INFORMATION: Synthesized

<400> SEQUENCE: 42

```
Arg Val Lys Phe Ser Arg Ser Ala Asp Ala Pro Ala Tyr Lys Gln Gly
 1               5                  10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                    85                  90                  95

Thr Lys Asp Thr Tyr Asp Ala Leu His Met Gln Ala Leu Pro Pro Arg
                100                 105                 110
```

<210> SEQ ID NO 43
<211> LENGTH: 242
<212> TYPE: PRT
<213> ORGANISM: Artificial Sequence
<220> FEATURE:
<223> OTHER INFORMATION: Synthesized

<400> SEQUENCE: 43

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
            35                  40                  45
```

```
Tyr His Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Tyr
                 85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Glu Val Gln Leu Val Glu
            115                 120                 125

Ser Gly Gly Gly Leu Val Gln Pro Gly Gly Ser Leu Arg Leu Ser Cys
130                 135                 140

Ala Ala Ser Gly Val Ser Leu Pro Asp Tyr Gly Val Ser Trp Val Arg
145                 150                 155                 160

Gln Ala Pro Gly Lys Gly Leu Glu Trp Val Ser Val Ile Trp Gly Ser
                165                 170                 175

Glu Thr Thr Tyr Tyr Asn Ser Ala Leu Lys Ser Arg Phe Thr Ile Ser
                180                 185                 190

Arg Asp Asn Ala Lys Asn Ser Leu Tyr Leu Gln Met Asn Ser Leu Arg
                195                 200                 205

Ala Glu Asp Thr Ala Val Tyr Tyr Cys Ala Lys His Tyr Tyr Tyr Gly
210                 215                 220

Gly Ser Tyr Ala Met Asp Tyr Trp Gly Gln Gly Thr Leu Val Thr Val
225                 230                 235                 240

Ser Ser

<210> SEQ ID NO 44
<211> LENGTH: 242
<212> TYPE: PRT
<213> ORGANISM: Artificial Sequence
<220> FEATURE:
<223> OTHER INFORMATION: Synthesized

<400> SEQUENCE: 44

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Lys Tyr
                 20                  25                  30

Leu Asn Trp Tyr Gln Gln Lys Pro Asp Gly Thr Val Lys Leu Leu Ile
             35                  40                  45

Tyr His Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr Gly Gly Gly Gly Ser
                100                 105                 110

Gly Gly Gly Gly Ser Gly Gly Gly Gly Ser Glu Val Lys Leu Gln Glu
            115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
```

-continued

```
                  165                 170                 175
Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 45
<211> LENGTH: 112
<212> TYPE: PRT
<213> ORGANISM: Homo sapiens

<400> SEQUENCE: 45

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

HUMANIZED ANTI-CD19 ANTIBODY AND USE THEREOF WITH CHIMERIC ANTIGEN RECEPTOR

CROSS-REFERENCE TO RELATED APPLICATION

This application is a divisional of U.S. patent application Ser. No. 16/600,064 filed Oct. 11, 2019, which is a division of U.S. patent application Ser. No. 15/876,538 filed Jan. 22, 2018, which is a continuation-in-part application of International application number PCT/CN2015/084991, filed Jul. 24, 2015, titled "HUMANIZED ANTI-CD19 ANTIBODY AND USE THEREOF WITH CHIMERIC ANTIGEN RECEPTOR," and a continuation-in-part application of International application number PCT/CN2017/070208, filed Jan. 5, 2017, titled "HUMANIZED ANTI-CD19 ANTIBODY AND USE THEREOF WITH CHIMERIC ANTIGEN RECEPTOR," which are hereby incorporated by reference in their entirety.

SEQUENCE LISTING

The Sequence Listing associated with this application is provided in text format in lieu of a paper copy and is hereby incorporated by reference into the specification. The name of the text file containing the Sequence Listing is Sequence_listing.txt.

TECHNICAL FIELD

This disclosure relates to biotechnology. More specifically, the disclosure relates to humanized antibodies and uses thereof.

BACKGROUND

CD19 is a hallmark of B-cells since CD19 is expressed on the surface of human B cells including pre-B cells, immature B cells, mature B cells and malignant B cells. CD19 has been used to diagnose cancers that arise from B cell (e.g., B-cell lymphomas). Further, some drugs associated with anti-CD19 may direct treatment specifically towards B-cell cancers. For example, CD19 monoclonal antibody may be used for the treatment of B-cell related diseases.

Monoclonal antibodies are typically made entirely from mouse cells. One problem with this is that the human immune system may see these antibodies as foreign and may mount a response against them. In the short term, this can sometimes cause an immune response. In the long term, this may cause the antibodies to only work the first time(s) they are given. After the first time, the human immune system may destroy these antibodies before the desired treatment takes place.

SUMMARY

Embodiments herein relate to a humanized antibody that binds to human CD19. The humanized antibody may include a heavy chain variable region (HVR) sequence including the amino acid sequence of SEQ ID NO: 27 and a light chain variable region (LVR) sequence including the amino acid sequences of SEQ ID NO: 34, the amino acid sequences of SEQ ID NO: 35, or the amino acid sequences of SEQ ID NO: 36.

In some embodiments, the HVR sequence may include at least one of a complementarity determining region (CDR) sequence of SEQ ID NO: 7, a CDR sequence of SEQ ID NO: 8, and a CDR sequence of SEQ ID NO: 9, and the HVR sequence may include a framework region (FR) sequence of SEQ ID NO: 24. In certain embodiments, the LVR sequence may include the amino acid sequences of SEQ ID NO: 34. In certain embodiments, the LVR sequence may include the amino acid sequences of SEQ ID NO: 35. In certain embodiments, the LVR sequence may include the amino acid sequences of SEQ ID NO: 36.

The embodiments further relate to a humanized antibody that binds to human CD19. The humanized antibody may include a heavy chain variable region (HVR) sequence including one of the amino acid sequences of SEQ ID NO: 25, SEQ ID NO: 26, or 27, and the humanized antibody may include a light chain variable region (LVR) sequence including one of the amino acid sequences of SEQ ID NO: 34, SEQ ID NO: 35, or SEQ ID NO: 36.

In some embodiments, the HVR sequence may include the amino acid sequence of SEQ ID NO: 27.

In some embodiments, the HVR sequence may include at least one of a complementarity determining region (CDR) sequence of SEQ ID NO: 7, a CDR sequence of SEQ ID NO: 8, and a CDR sequence of SEQ ID NO: 9.

In some embodiments, the HVR sequence may include a framework region (FR) sequence of SEQ ID NO: 24.

In some embodiments, the LVR sequence may include the amino acid sequences of SEQ ID NO: 34.

In some embodiments, the LVR sequence may include the amino acid sequences of SEQ ID NO: 35.

In some embodiments, the LVR sequence may include the amino acid sequences of SEQ ID NO: 36.

In some embodiments, the HVR is joined to a human IgG chain constant region. In these instances, the human IgG may include IgG1 or IgG3.

In some embodiments, the humanized antibody may include a conjugated to a cytotoxic agent. In these instances, the cytotoxic agent may include a radioactive isotope or a toxin.

In some embodiments, the humanized antibody may be conjugated to a sequence derived from 4-1 BB or CD28, or a combination thereof.

In some embodiments, the humanized antibody or fragment may be produced in an HEK293 cell.

In some embodiments, the humanized antibody or fragment may be produced in an HEK293 cell, a B cell, a T cell, an NK cell, an embryonic cell, a dendritic cell or a macrophage.

The embodiments herein further relate to a composition including the humanized antibody and a pharmaceutically acceptable carrier.

The embodiments herein further relate to an article of manufacture including a container and a composition contained therein. The composition may include the humanized antibody.

The embodiments herein further relate to a polynucleotide that encodes the humanized antibody.

The embodiments herein further relate to an expression vector encoding the humanized antibody.

The embodiments herein further relate to a host cell including a nucleic acid encoding the humanized antibody.

The embodiments herein further relate to a method of treating a CD19 positive tumor. The method may include administering to a subject having a CD19 positive tumor a therapeutically effective amount of the humanized antibody.

The embodiments herein further relate to a method of treating an autoimmune disease. The method may include administering to a subject having an autoimmune disease a therapeutically effective amount of the humanized antibody.

The embodiments herein further relate to a method of treating a CD19 related disorder. The method may include administering to a subject having an autoimmune disease a therapeutically effective amount of the humanized antibody or fragment. In some embodiments, the CD19 related disorder may include at least one of a B-cell lymphoma, leukemia or an autoimmune disease in a subject.

The embodiments herein further relate to a modified cell including a chimeric antigen receptor (CAR) that includes an antigen recognition domain and an intracellular domain. The antigen domain may include the humanized antibody.

The embodiments herein further relate to a method for treating a subject having a CD19 positive tumor. The method may include administering a modified cell to the subject having the CD19 positive tumor. The modified cell may include an intracellular domain and an antigen recognition domain that includes the humanized antibody.

In some embodiments, the modified cell may include at least one of a B cell, a T cell, an NK cell, an embryonic cell, a dendritic cell or a macrophage.

In some embodiments, the genetically modified cell replicates in vivo.

In some embodiments, the modified cell may form memory cells in the subject.

In some embodiments, the modified cells are administered intravenously to the subject.

In some embodiments, the modified cells persist in the subject.

In some embodiments, the modified cell is an autologous T cell.

In some embodiments, the modified cell produces the humanized antibody and/or an intracellular domain.

Some embodiments relate to a human T cell including a nucleic acid sequence encoding a CAR. For example, the CAR may include a CD19 antigen binding domain including the amino acid sequence of SEQ ID NO:37. In some embodiments, the CAR may further include a transmembrane domain, and an intracellular domain and a signaling domain of a costimulatory molecule.

In some embodiments, the intracellular domain may include a CD3-zeta signaling domain.

In some embodiments, the antigen binding fragment is a scFv. For example, the scFv may include the amino acid sequence of SEQ ID NO:37.

In some embodiments, the T cell comprises a vector that comprises the nucleic acid sequence. For example, the vector is a lentiviral vector.

In some embodiments, a pharmaceutical composition comprising the human T cell as described above.

Some embodiments relate to an isolated nucleic acid sequence encoding a humanized antibody or antigen binding fragment thereof, wherein the humanized antibody or antigen binding fragment thereof comprising a heavy chain variable (HCV) sequence having the amino acid sequence of SEQ ID NO: 27, or a light chain variable (LCV) sequence having the amino acid sequence of SEQ ID NO: 34, 35, 36, or 37, or a combination thereof.

Some embodiments relate to an expression vector comprising the isolated nucleic acid sequence operably linked to control sequences recognized by a host cell transfected with the vector.

Some embodiments relate to a host cell comprising the expression vector.

In some embodiments, the antigen binding fragment is selected from the group consisting of a Fab, Fab', Fab'-SH, Fv, scFv, F(ab)2 and a diabody.

In some embodiments, the humanized antibody or antigen binding fragment thereof comprises the HCV sequence having the amino acid sequence of SEQ ID NO: 27 and the LCV sequence having the amino acid sequence of SEQ ID NO: 37.

In some embodiments, the humanized antibody or antigen binding fragment thereof is a scFv.

Some embodiments relate to a CAR comprising the scFv 8. In some embodiments, the CAR comprises an antigen binding domain, a transmembrane domain, a costimulatory signaling region, and a CD3 zeta signaling domain, and the antigen binding domain binds to CD19.

In some embodiments, the antigen binding domain comprises the amino acid sequences of SEQ ID NOs: 43.

In some embodiments, the CD3 zeta signaling domain comprises the amino acid sequence of SEQ ID NO: 42 or 45.

In some embodiments, the costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

Some embodiments relate to a vector comprising a nucleic acid sequence encoding the CAR, a cell comprising the CAR. For example, the cell is a T cell or an NK cell. Some embodiments relate to a composition comprising a population of the cell, and the cell is a T cell.

Some embodiments relate to a method for treating a tumor expressing CD19, the method comprising: administrating to a subject the composition described above.

Some embodiments relate to a method for stimulating an anti-tumor immune response to a tumor expressing CD19, the method comprising administrating to a subject an effective amount of a pharmaceutical composition comprising a population of the cell described above.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The detailed description is described with reference to the accompanying figures.

FIG. 2 illustrates a sequence alignment comparing the amino acid sequences of variable domains of the light chain of L2D8 (SEQ ID: 34), L2D12 (SEQ ID: 35), and L5F3 (SEQ ID: 36).

FIGS. 8-10 show the vectors for expression of one or more polynucleotides in host cells in accordance with embodiments herein.

DETAILED DESCRIPTION

Figure 1:
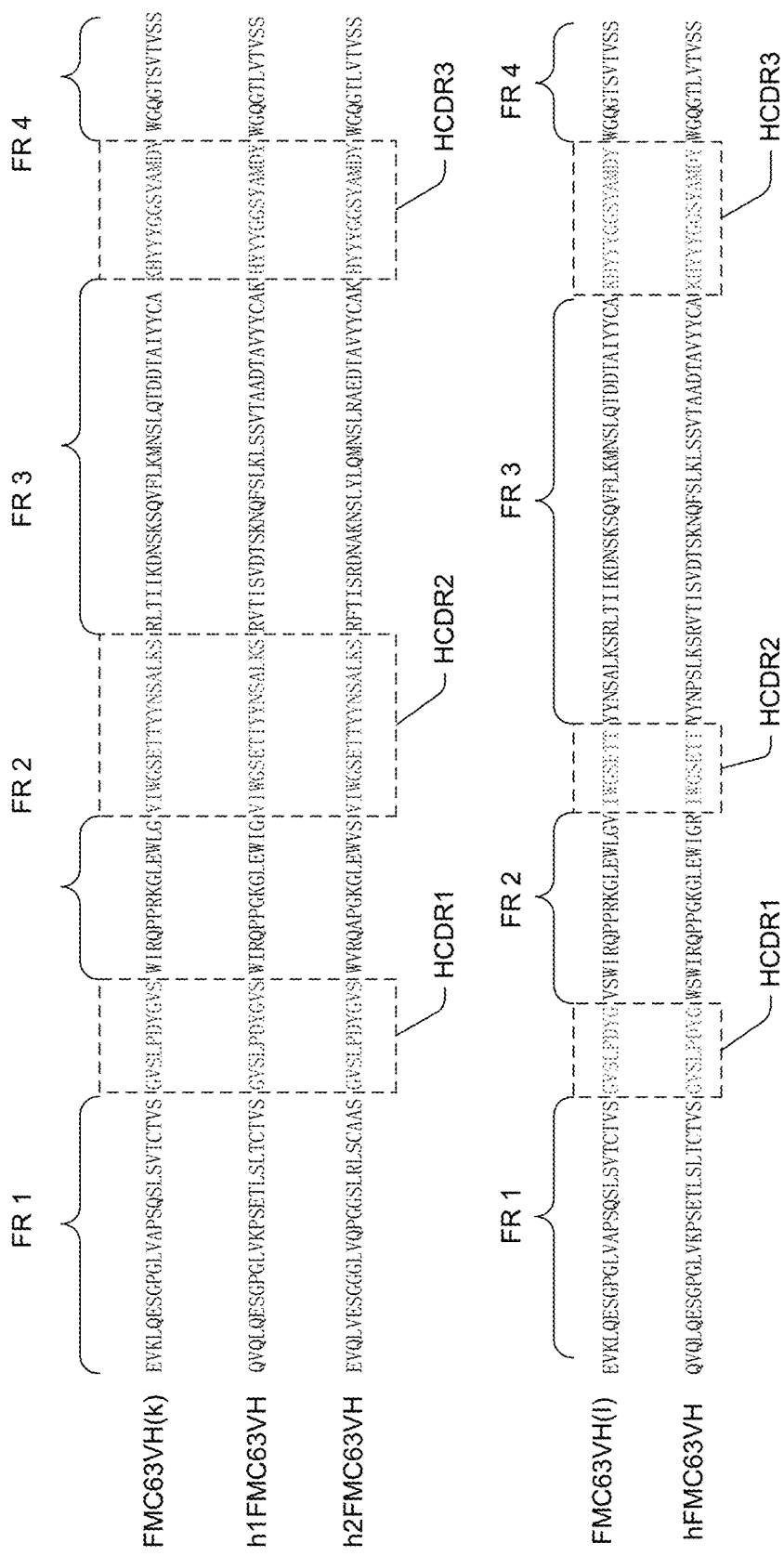
FIG. 1 illustrates a sequence alignment comparing the amino acid sequences of each variable domains of the heavy chain of FMC63VH (SEQ ID: 1), hFMC63VH (SEQ ID: 25), h1FMC63VH (SEQ ID: 26), and h2FMC63VH (SEQ ID: 27) according to Kabat or IMGT database definitions.

Unless defined otherwise, all technical and scientific terms used herein have the same meaning as commonly understood by those of ordinary skill in the art to which the present disclosure belongs. Although any methods and materials similar or equivalent to those described herein can be used in the practice or testing of the present disclosure, methods, and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises" and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but those other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence of a peptide or protein; or (b) a peptide or polypeptide having an amino acid sequence that is substantially identical to a sequence of amino acids in a reference peptide or protein.

As used herein, the terms "function" and "functional" and the like refer to a biological, binding, or therapeutic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, Nucleic Acids Research 12, 387-395) which is incorporated herein by reference. In this way, sequences of a similar or substantially different length to those cited herein could be compared by insertion of gaps into the alignment, such gaps being determined, for example, by the comparison algorithm used by GAP.

The term "host cell" includes an individual cell or cell culture which can be or has been a recipient of any recombinant vector(s) or isolated polynucleotide of the present disclosure. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the present disclosure. A host cell which comprises a recombinant vector of the present disclosure is a recombinant host cell. For example, a cell that produces a humanized CD19 antibody of the present disclosure will include the bacterial and eukaryotic host cells into which nucleic acid encoding the antibodies have been introduced.

An "isolated" antibody is one which has been identified and separated and/or recovered from a component of its natural environment. Contaminant components of its natural environment are materials which would interfere with diagnostic or therapeutic uses for the antibody and may include enzymes, hormones, and other proteinaceous or non proteinaceous solutes.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules, therefore, are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA fora presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The recitation "polynucleotide" or "nucleic acid" as used herein designates mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes single and double stranded forms of DNA and RNA.

The terms "polynucleotide variant" and "variant" and the like refer to polynucleotides displaying substantial sequence identity with a reference polynucleotide sequence or polynucleotides that hybridize to a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs that encode these enzymes.

"Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally occurring amino acid polymers. In certain aspects, polypeptides may include enzymatic polypeptides, or "enzymes," which typically catalyze (i.e., increase the rate of) various chemical reactions.

The recitation polypeptide "variant" refers to polypeptides that are distinguished from a reference polypeptide sequence by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard; it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The term "reference sequence" generally refers to a nucleic acid coding sequence, or amino acid sequence, to which another sequence is being compared. All polypeptide and polynucleotide sequences described herein are included as references sequences.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 97%, 98%, 99% or 100% sequence identity to any of the reference sequences described herein (see, e.g., Sequence Listing), typically where the polypeptide variant maintains at least one biological activity of the reference polypeptide.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less.

"Substantially" or "essentially" means nearly totally or completely, for instance, 95%, 96%, 97%, 98%, 99% or greater of some given quantity.

"Treating" or "treatment" or "alleviation" refers to both therapeutic treatment and prophylactic or preventative measures, wherein the object is to prevent or slow down (lessen) the targeted pathologic condition or disorder. For example, a subject is successfully "treated" for a CD19 positive cancer or an autoimmune disease if, after receiving a therapeutic amount of a CD19 antibody or other compositions associated with CD19 antibody of the present disclosure according to the methods of the present disclosure, the subject shows observable and/or measurable reduction in or absence of one or more signs and symptoms of the particular disease. For example, for cancer, reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Reduction of the signs or symptoms of a disease may also be felt by the patient. Treatment can achieve a complete response, defined as disappearance of all signs of cancer, or a partial response, wherein the size of the tumor is decreased, preferably by more than 50 percent, more preferably by 75%. A patient is also considered treated if the patient experiences stable disease. In some embodiment, the cancer patients are still progression-free in cancer after one year, preferably after 15 months. These parameters for assessing successful treatment and improvement in the disease are readily measurable by routine procedures familiar to a physician of appropriate skill in the art.

The terms "modulating" and "altering" include "increasing" and "enhancing" as well as "decreasing" or "reducing," typically in a statistically significant or a physiologically significant amount or degree relative to control. In specific embodiments, immunological rejection associated with transplantation of the blood substitutes is decreased relative to an unmodified or differently modified stem cell by at least 10%, at least 15%, at least 20%, at least 25%, at least 30%, at least 40%, at least 50%, at least 60%, at least 70%, at least 80%, at least 90%, at least 100%, at least 150%, at least 200%, at least 300%, at least 400%, at least 500%, or at least 1000%.

An "increased" or "enhanced" amount is typically a "statistically significant" amount, and may include an increase that is 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

A "decreased" or "reduced" or "lesser" amount is typically a "statistically significant" amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

By "obtained from" is meant that a sample such as, for example, a polynucleotide or polypeptide is isolated from, or derived from, a particular source, such as the desired organism or a specific tissue within the desired organism. "Obtained from" can also refer to the situation in which a polynucleotide or polypeptide sequence is isolated from, or derived from, a particular organism or tissue within an organism. For example, a polynucleotide sequence encoding a reference polypeptide described herein may be isolated from a variety of prokaryotic or eukaryotic organisms, or from particular tissues or cells within a certain eukaryotic organism. A "therapeutically effective amount" refers to an amount of an antibody or a drug effective to "treat" a disease or disorder in a subject. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See preceding definition of "treating."

"Chronic" administration refers to administration of the agent(s) in a continuous mode as opposed to an acute mode, so as to maintain the initial therapeutic effect (activity) for an extended period of time. "Intermittent" administration is a treatment that is not consecutively done without interruption, but rather is cyclic in nature.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the present disclosure, in bacterial or eukaryotic cells. Suitable vectors are disclosed below.

Embodiments herein relate to humanized antibodies and the user thereof. The embodiments further relate to a humanized antibody that binds to human CD19.

The CD19 antigen is an antigen of about 90 kDa identified, for example, by the HD237 or B4 antibody (Kiesel et al., Leukemia Research II, 12:1119 (1987)). CD19 is found on cells throughout differentiation of B-lineage cells from the stem cell stage through terminal differentiation into plasma cells, including but not limited to, pre-B cells, B cells (including naïve B cells, antigen-stimulated B cells, memory B cells, plasma cells, and B lymphocytes) and follicular dendritic cells. CD19 is also found on B cells in human fetal tissues. In some embodiments, the CD19 antigen targeted by the antibodies of the present disclosure is the human CD19 antigen.

The term "antibody" is used in the broadest sense and specifically covers monoclonal antibodies (including full-length monoclonal antibodies), multispecific antibodies (e.g., bispecific antibodies), and antibody fragments so long as they exhibit the desired biological activity or function.

The biological activity of the CD19 binding and humanized CD19 binding antibodies of the present disclosure will include at least binding of the antibody to human CD19, and/or binding to human and other primate CD19 (including cynomolgus monkey, rhesus monkey, chimpanzees). Typically, the C19 binding agent binds with an affinity of at least about $1 \times 10^{-7}$ M, and preferably $10^{-8}$ M to $10^{-9}$ M, $10^{-10}$ M, $10^{-11}$ M, or $10^{-12}$ M and binds to the predetermined antigen with an affinity that is at least two-fold greater than its affinity for binding to a non-specific antigen (e.g., BSA, casein) other than the predetermined antigen or a closely-related antigen.

"Antibody fragments" comprise a portion of a full-length antibody, generally the antigen-binding or variable region of the antibody. Examples of antibody fragments include Fab, Fab', F(ab')2, and Fv fragments; diabodies; linear antibodies; single-chain antibody molecules (e.g., scFv); and multispecific antibodies formed from antibody fragments.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of a Fv comprising only three complementarity determining regions (CDRs) specific for an antigen) has the ability to recognize and bind antigen, although at a lower affinity than the entire binding site.

A monoclonal antibody as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies and is not to be construed as requiring the production of the antibody by any particular method. For example, the monoclonal antibodies to be used in accordance with the present disclosure may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature 352:624-628 (1991) and Marks et al., J. Mol. Biol. 222:581-597 (1991), for example.

Functional fragments of the CD19 binding antibodies of the present disclosure are those fragments that retain binding to CD19 with substantially the same affinity as the intact full-length molecule from which they are derived and show biological activity including depleting B cells as measured by in vitro or in vivo assays such as those described herein.

Variable refers to the fact that certain segments of the variable domains (V domains) differ extensively in sequence among antibodies. The V domain mediates antigen binding and defines the specificity of a particular antibody for its particular antigen. However, the variability is not evenly distributed across the 10-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen but exhibit various effector functions, such as participation of the antibody in antibody-dependent cellular cytotoxicity (ADCC).

Hypervariable region refers to the amino acid residues of an antibody which are responsible for antigen-binding. The hypervariable region generally comprises amino acid residues from a CDR (e.g. around about residues 24-34 (L1), 50-56 (L2) and 89-97 (L3) in the VL, and around about 31-35B (H1), 50-65 (H2) and 95-102 (H3) in the VH (Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the VL, and 26-32 (H1), 52A-55 (H2) and 96-101 (H3) in the VH (Chothia and Lesk J. Mol. Biol. 196:901-917 (1987)).

Chimeric antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. Proc. Natl Acad. Sci. USA 81:6851-6855 (1984)). Humanized antibody as used herein is a subset of chimeric antibodies.

Humanized forms of non-human (e.g., murine) antibodies are chimeric antibodies which contain minimal sequence derived from non-human immunoglobulin. In some embodiments, humanized antibodies are human immunoglobulins (recipient or acceptor antibody) in which hypervariable region residues of the recipient are replaced by hypervariable region residues from a non-human species (donor antibody) such as a mouse, rat, rabbit or nonhuman primate having the desired specificity, affinity, and capacity. In some embodiments, humanized antibodies are antibodies derived from human cells or from transgenic animals (typically mice) with express human antibody genes.

In some embodiments, the humanized antibody may include a heavy chain variable region (HVR) sequence comprising one of the amino acid sequences of SEQ ID NO: 25, SEQ ID NO: 26, or 27, and the humanized antibody may include a light chain variable region (LVR) sequence including one of the amino acid sequences of SEQ ID NO: 34, SEQ ID NO: 35, or SEQ ID NO: 36.

In some embodiments, the HVR sequence may include the amino acid sequence of SEQ ID NO: 27. In these instances, the HVR sequence may include at least one of a complementarity determining region (CDR) sequence of SEQ ID NO: 7, a CDR sequence of SEQ ID NO: 8, and a CDR sequence of SEQ ID NO: 9.

In some embodiments, the HVR sequence may include a framework region (FR) sequence of SEQ ID NO: 24. In these instances, the LVR sequence may include at least one of the amino acid sequences of SEQ ID NO: 34, the amino acid sequences of SEQ ID NO: 35, or the amino acid sequences of SEQ ID NO: 36.

In some embodiments, the HVR is joined to a human IgG chain constant region. In these instances, the human IgG is IgG1 or IgG3.

In some embodiments, the humanized antibody may include a conjugated to a cytotoxic agent. In these instances, the cytotoxic agent may include a radioactive isotope or a toxin.

Cytotoxic agent may include a substance that inhibits or prevents the function of cells and/or causes the destruction of cells. The term is intended to include radioactive isotopes (e.g., I131, I125, Y90 and Re186), chemotherapeutic agents, and toxins such as enzymatically active toxins of bacterial, fungal, plant or animal origin, or fragments thereof.

In some embodiments, the humanized antibody is conjugated to a sequence derived from 4-1 BB or CD28, or a combination thereof. The humanized antibody or fragment may be produced in an HEK293 cell, a B cell, a T cell, an NK cell, an embryonic cell, a dendritic cell or a macrophage.

The embodiments herein further relate to one or more compositions that include the humanized antibody. The one or more compositions may further include a pharmaceutically acceptable carrier and/or a container containing the humanized antibody.

The embodiments herein further relate to a polynucleotide that encodes the humanized antibody, an expression vector encoding the humanized antibody, and/or a host cell containing a nucleic acid encoding the humanized antibody.

The embodiments herein further relate to a method of treating a CD19 related disease. The method includes administering to a subject having the CD19 disease a therapeutically effective amount of the humanized antibody. The CD19 disease may include at least one of CD19 positive tumors, a B-cell lymphoma or leukemia, and/or an autoimmune disease in the subject.

B cell depletion refers to a reduction in B cell levels in an animal or human after drug or antibody treatment, as compared to the B cell level before treatment. B cell levels are measurable using well-known assays such as those described in the Experimental Examples. B cell depletion can be complete or partial. In one embodiment, the depletion of CD19 expressing B cells is at least 25%. Not to be limited by any one mechanism, possible mechanisms of B-cell depletion include ADCC, CDC, apoptosis, modulation of calcium flux, or a combination of two or more of the preceding.

An autoimmune disease may refer to a non-malignant disease or disorder arising from and directed against an individual's own (self) antigens and/or tissues.

The embodiments herein further relate to a method for treating a subject having a CD19 positive tumor. The method includes administering a modified cell to the subject having the CD19 positive tumor. In some embodiments, the modified cell may produce and/or contain an antigen recognition domain having the humanized antibody and an intracellular domain. In these instances, the modified cell may include at least one of a B cell, a T cell, an NK cell, an embryonic cell, a dendritic cell or a macrophage. This genetically modified cell may obtain from memory cells in the subject and replicates in vivo. The modified cells are administered intravenously to the subject and persist in the subject. In some embodiments, the modified cell is an autologous T cell.

Some embodiments relate to a human T cell including a nucleic acid sequence encoding a CAR. For example, the CAR may include a CD19 antigen binding domain including the amino acid sequence of SEQ ID NO:37. In some embodiments, the CAR may further include a transmembrane domain, and an intracellular domain and a signaling domain of a costimulatory molecule.

In some embodiments, the intracellular domain may include a CD3-zeta signaling domain.

In some embodiments, the antigen binding fragment is a scFv. For example, the scFv may include the amino acid sequence of SEQ ID NO:37.

In some embodiments, the T cell comprises a vector that comprises the nucleic acid sequence. For example, the vector is a lentiviral vector.

In some embodiments, a pharmaceutical composition comprising the human T cell as described above.

CARs are molecules generally including an extracellular and intracellular domain. The extracellular domain includes a target-specific binding element. The intracellular domain (e.g., cytoplasmic domain) includes a costimulatory signaling region and a zeta chain portion. The costimulatory signaling region refers to a portion of the CAR including the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain of the polypeptide chain. A spacer domain may include up to 300 amino acids, preferably 10 to 100 amino acids and most preferably 25 to 50 amino acids.

In some embodiments, the target-specific binding element of the CAR in the present disclosure may recognize a tumor antigen. Tumor antigens are proteins that are produced by tumor cells that elicit an immune response, particularly T-cell mediated immune responses. Tumor antigens are well known in the art and include, for example, a glioma-associated antigen, carcinoembryonic antigen (CEA), β-human chorionic gonadotropin, alpha-fetoprotein (AFP), lectin-reactive AFP, thyroglobulin, RAGE-1, MN-CA IX, human telomerase reverse transcriptase, RU1, RU2 (AS), intestinal carboxylesterase, mut hsp70-2, M-CSF, prostase, prostate-specific antigen (PSA), PAP, NY-ESO-1, LAGE-1a, p53, prostein, PSMA, Her2/neu, survivin and telomerase, prostate carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In some embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8, or viral-associated antigens expressed by the tumor.

In some embodiments, the antigen binding element of the CAR of the disclosure targets CD19. In some instances, the antigen binding element of the CAR of the disclosure includes anti-CD19 scFV including the amino acid sequence of SEQ ID NO: 37.

Some embodiments relate to an isolated nucleic acid sequence encoding a humanized antibody or antigen binding fragment thereof, wherein the humanized antibody or antigen binding fragment thereof comprising a heavy chain variable (HCV) sequence having the amino acid sequence of SEQ ID NO: 27, or a light chain variable (LCV) sequence having the amino acid sequence of SEQ ID NO: 34, 35, 36, or 37, or a combination thereof.

Some embodiments relate to an expression vector comprising the isolated nucleic acid sequence operably linked to control sequences recognized by a host cell transfected with the vector.

Some embodiments relate to a host cell comprising the expression vector.

In some embodiments, the antigen binding fragment is selected from the group consisting of a Fab, Fab', Fab'-SH, Fv, scFv, F(ab)2 and a diabody.

In some embodiments, the humanized antibody or antigen binding fragment thereof comprises the HCV sequence having the amino acid sequence of SEQ ID NO: 27 and the LCV sequence having the amino acid sequence of SEQ ID NO: 37.

In some embodiments, the humanized antibody or antigen binding fragment thereof is a scFv.

Some embodiments relate to a CAR comprising the scFv 8. In some embodiments, the CAR comprises an antigen binding domain, a transmembrane domain, a costimulatory signaling region, and a CD3 zeta signaling domain, and the antigen binding domain binds to CD19.

In some embodiments, the antigen binding domain comprises the amino acid sequences of SEQ ID NOs: 43.

In some embodiments, the CD3 zeta signaling domain comprises the amino acid sequence of SEQ ID NO: 42 or 45.

In some embodiments, the costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

Some embodiments relate to a vector comprising a nucleic acid sequence encoding the CAR, a cell comprising the CAR. For example, the cell is a T cell or an NK cell. Some embodiments relate to a composition comprising a population of the cell, and the cell is a T cell.

Some embodiments relate to a method for treating a tumor expressing CD19, the method comprising: administrating to a subject the composition described above.

Some embodiments relate to a method for stimulating an anti-tumor immune response to a tumor expressing CD19, the method comprising administrating to a subject an effective amount of a pharmaceutical composition comprising a population of the cell described above.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The embodiments of the present disclosure further relate to vectors in which a DNA of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from oncoretroviruses such as murine leukemia viruses in that they can transduce non-proliferating cells, such as hepatocytes. They also have the added advantage of low immunogenicity.

The expression of natural or synthetic nucleic acids encoding CARs is typically achieved by operably linking a nucleic acid encoding the CAR polypeptide or portions thereof to one or more promoters and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

Additional information related to expression synthetic nucleic acids encoding CARs and gene transfer into mammalian cells is provided in U.S. Pat. No. 8,906,682, incorporated by reference in its entirety.

The embodiments further relate to methods for treating a patient for illness including administering to the patient an effective amount of the engineered cells of the present disclosure. Various illnesses can be treated according to the present methods including cancer, such as ovarian carcinoma, breast carcinoma, colon carcinoma, glioblastoma multiforme, prostate carcinoma and leukemia. In some embodiments, the method includes administering to a human patient a pharmaceutical composition including an effective antitumor amount of a population of human T cells, wherein the human T cells of the population include human T cells that comprise the nucleic acid sequence as described in the present disclosure.

Cancers that may be treated include tumors that are not vascularized, or not yet substantially vascularized, as well as vascularized tumors. The cancers may include non-solid tumors (such as hematological tumors, for example, leukemias and lymphomas) or may include solid tumors. Types of cancers to be treated with the CARs of the disclosure include, but are not limited to, carcinoma, blastoma, and sarcoma, and certain leukemia or lymphoid malignancies, benign and malignant tumors, and malignancies, e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyngioma, ependymoma, pinealoma, hemangioblastoma, acoustic neuroma, oligodendroglioma, meningioma, neuroblastoma, retinoblastoma and brain metastases).

Generally, the cells activated and expanded as described herein may be utilized in the treatment and prevention of diseases that arise in individuals who are immunocompromised. In particular, the engineered cells of the present disclosure are used in the treatment of cancer. In certain embodiments, the cells of the present disclosure are used in the treatment of patients at risk of developing cancer. Thus, the present disclosure provides methods for the treatment or prevention of cancer comprising administering to a subject in need thereof, a therapeutically effective amount of the engineered T cells of the present disclosure.

The engineered T cells of the present disclosure may be administered either alone or as a pharmaceutical composition in combination with diluents and/or with other components such as IL-2 or other cytokines or cell populations. Briefly, pharmaceutical compositions of the present disclosure may include a target cell population as described herein, in combination with one or more pharmaceutically or physiologically acceptable carriers, diluents or excipients. Such compositions may include buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "a tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of 104 to 109 cells/kg body weight, preferably 105 to 106 cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regimen for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have apheresis performed), activate T cells therefrom according to the present disclosure, and reinfuse the patient with these activated and expanded T cells. This process can be carried out multiple times every few weeks. In certain embodiments, T cells can be activated from blood draws off from 10 ccs to 400 ccs. In certain embodiments, T cells are activated from blood draws of 20 cc, 30 ccs, 40 ccs, 50 ccs, 60 ccs, 70 ccs, 80 ccs, 90 ccs, or 100 ccs. Not to be bound by theory, using this multiple blood draw/multiple reinfusion protocols, may select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i. v.) injection, or intraperitoneally. In one embodiment, the T cell compositions of the present disclosure are administered to a patient by intradermal or subcutaneous injection. In another embodiment, the T cell compositions of the present disclosure are preferably administered by i.v. injection. The compositions of T cells may be injected directly into a tumor, lymph node, or site of infection.

In certain embodiments of the present disclosure, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the present disclosure may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, Cytoxan, fludarabine, cyclosporine, FK506, rapamycin, mycophenolic acid, steroids, FR901228, cytokines, and irradiation. These drugs inhibit either the calcium-dependent phosphatase calcineurin (cyclosporine and FK506) or inhibit the p70S6 kinase that is important for growth factor-induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In a further embodiment, the cell compositions of the present disclosure are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present disclosure are administered following B-cell ablative therapy such as agents that react with CD20, e.g., Rituxan. For example, in one embodiment, subjects may undergo standard treatment with high-dose chemotherapy followed by peripheral blood stem cell transplantation. In certain embodiments, following the transplant, subjects receive an infusion of the expanded immune cells of the present disclosure. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period of 1 and 30 days. The preferred daily dose is 1 to 10 mg per day although, in some instances, larger doses of up to 40 mg per day may be used (described in U.S. Pat. No. 6,120,766, incorporated by reference in its entirety).

Additional information on the methods of cancer treatment using engineer T cells is provided in U.S. Pat. No. 8,906,682, incorporated by reference in its entirety.

CARs are molecules generally including an extracellular and intracellular domain. The extracellular domain includes a target-specific binding element. The intracellular domain (e.g., cytoplasmic domain) includes a costimulatory signaling region and a zeta chain portion. The costimulatory signaling region refers to a portion of the CAR including the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain of the polypeptide chain. A spacer domain may include up to 300 amino acids, preferably 10 to 100 amino acids, and most preferably 25 to 50 amino acids.

In some embodiments, the target-specific binding element of the CAR in the present disclosure may recognize a tumor antigen. Tumor antigens are proteins that are produced by tumor cells that elicit an immune response, particularly T-cell mediated immune responses. Tumor antigens are well known in the art and include, for example, a glioma-associated antigen, carcinoembryonic antigen (CEA), β-human chorionic gonadotropin, alpha-fetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In some embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 514, Fetal AchR, NKG2D ligands, CD44v6, TEM1, TEM8, or viral-associated antigens expressed by the tumor.

In some embodiments, the binding element of the CAR may include an antigen binding moiety that when bound to its cognate antigen, affects a tumor cell such that the tumor cell fails to grow, or is promoted to die or diminish.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The embodiments of the present disclosure further relate to vectors in which a DNA of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from oncoretroviruses such as murine leukemia viruses in that they can transduce non-proliferating cells, such as hepatocytes. They also have the added advantage of low immunogenicity.

The expression of natural or synthetic nucleic acids encoding CARs is typically achieved by operably linking a nucleic acid encoding the CAR polypeptide or portions thereof to one or more promoters and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The embodiments further relate to methods for treating a patient for illness including administering to the patient an effective amount of the engineered cells of the present disclosure. Various illnesses can be treated according to the present methods including cancer, such as ovarian carcinoma, breast carcinoma, colon carcinoma, glioblastoma multiforme, prostate carcinoma and leukemia. In some embodiments, the method includes administering to a human patient a pharmaceutical composition including an antitumor effective amount of a population of human T cells, wherein the human T cells of the population include human T cells that comprises the nucleic acid sequence as described in the present disclosure.

Cancers that may be treated include tumors that are not vascularized, or not yet substantially vascularized, as well as vascularized tumors. The cancers may include non-solid tumors (such as hematological tumors, for example, leukemias and lymphomas) or may include solid tumors. Types of cancers to be treated with the CARs of the disclosure include, but are not limited to, carcinoma, blastoma, and sarcoma, and certain leukemia or lymphoid malignancies, benign and malignant tumors, and malignancies, e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brain stem glioma and mixed gliomas), glioblastoma (also known as glioblastoma multiforme) astrocytoma, CNS lymphoma, germinoma, medulloblastoma, Schwannoma craniopharyngioma, ependymoma, pinealoma, hemangioblastoma, acoustic neuroma, oligodendroglioma, meningioma, neuroblastoma, retinoblastoma and brain metastases).

Generally, the cells activated and expanded as described herein may be utilized in the treatment and prevention of diseases that arise in individuals who are immunocompromised. In particular, the engineered cells of the present disclosure are used in the treatment of cancer. In certain embodiments, the cells of the present disclosure are used in the treatment of patients at risk of developing cancer. Thus, the present disclosure provides methods for the treatment or prevention of cancer comprising administering to a subject in need thereof, a therapeutically effective amount of the engineered T cells of the present disclosure.

The engineered T cells of the present disclosure may be administered either alone or as a pharmaceutical composition in combination with diluents and/or with other components such as IL-2 or other cytokines or cell populations. Briefly, pharmaceutical compositions of the present disclosure may include a target cell population as described herein, in combination with one or more pharmaceutically or physiologically acceptable carriers, diluents or excipients. Such compositions may include buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an antitumor effective amount", "a tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regimen for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have apheresis performed), activate T cells therefrom according to the present disclosure, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocols, may select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i. v.) injection, or intraperitoneally. In one embodiment, the T cell compositions of the present disclosure are administered to a patient by intradermal or subcutaneous injection. In another embodiment, the T cell compositions of the present disclosure are preferably administered by i.v. injection. The compositions of T cells may be injected directly into a tumor, lymph node, or site of infection.

In certain embodiments of the present disclosure, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the present disclosure may be used in combination with chemotherapy, radiation, immunosuppressive agents, such as cyclosporin, azathioprine, methotrexate, mycophenolate, and FK506, antibodies, or other immunoablation agents such as CAM PATH, anti-CD3 antibodies or other antibody therapies, Cytoxan, fludarabine, cyclosporin, FK506, rapamycin, mycophenolic acid, steroids, FR901228, cytokines, and irradiation. These drugs inhibit either the calcium-dependent phosphatase calcineurin (cyclosporine and FK506) or inhibit the p70S6 kinase that is important for growth factor-induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In a further embodiment, the cell compositions of the present disclosure are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present disclosure are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present disclosure. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766, incorporated by reference in its entirety).

Additional information on the methods of cancer treatment using engineer T cells is provided in U.S. Pat. No. 8,906,682, incorporated by reference in its entirety.

Some embodiments relate to an in vitro method for preparing modified cells. The method may include obtaining a sample of cells from the subject. For example, the sample may include T-cells or T-cell progenitors. The method may further include transfecting the cells with a DNA encoding at least a CAR, culturing the population of CAR cells ex vivo in a medium that selectively enhances proliferation of CAR-expressing T-cells.

In some embodiments, the sample is a cryopreserved sample.

In some embodiments, the sample of cells is from umbilical cord blood.

In some embodiments, the sample of cells is a peripheral blood sample from the subject.

In some embodiments, the sample of cells was obtained by apheresis.

In some embodiments, the sample of cells was obtained by venipuncture.

In some embodiments, the sample of cells is a subpopulation of T-cells.

In some embodiments, genes of the CAR cells associated with an endogenous T-cell receptor and/or endogenous HLA are distorted such that immunogenicity of the CAR cells is reduced.

The various embodiments described above can be combined to provide further embodiments. These and other changes can be made to the embodiments in light of the above-detailed description.

The present disclosure is further illustrated by the following specific examples. The examples are provided for illustration only and should not be construed as limiting the scope of the disclosure in any way.

Examples

Recombinant Human CD19 Antigen and Anti-CD19 Murine Monoclonal Antibody

Recombinant anti-human CD19 murine antibody (FMC63) was prepared. Genes of variable domains of the heavy chain (SEQ ID NO: 1) and variable domains of light chains (SEQ ID NO: 2) were obtained and further optimized to obtain various polynucleotides encoding FMC63. Gene optimization includes eliminations of *E. coli* rare codons and eliminations of restriction sites used by related eukaryotic expression systems and phage display systems. Accordingly, recombinant polynucleotides (FMC63VH) encoding heavy chains of FMC63 (FMC63VH) and recombinant polynucleotides (FMC63VK) encoding light chains of FMC63 (FMC63VK) were designed and synthesized (See Table 1).

TABLE 1

| Name | Sequence | SEQ ID NO |
|---|---|---|
| FMC63VH | EVKLQESGPGLVAPSQSLSVTCTVSGVSLPDYGVSWIRQPPRKGL EWLGVIWGSETTYYNSALKSRLTIIKDNSKSQVFLKMNSLQTDDT AIYYCAKHYYYGGSYAMDYWGQGTSVTVSS | 3 |
| FMC63VK | DIQMTQTTSSLSASLGDRVTISCRASQDISKYLNWYQQKPDGTVK LLIYHTSRLHSGVPSRFSGSGSGTDYSLTISNLEQEDIATYFCQQ GNTLPYTFGGGTKLEIK | 4 |
| FMC63VH | GAGGTGAAACTGCAGGAGTCAGGACCTGGCCTGGTGGCGCCA TCACAGAGCCTGTCCGTCACATGCACTGTCTCAGGGGTCTCAT TACCTGACTATGGTGTAAGCTGGATTCGCCAGCCTCCACGCAA GGGTCTGGAGTGGCTGGGAGTAATCTGGGGTAGTGAAACCAC ATACTATAATTCAGCTCTCAAATCCCGCCTGACCATCATCAAGG ACAACTCCAAGAGCCAAGTTTTCTTAAAAATGAACAGTCTGCA AACTGATGACACAGCCATTTACTACTGTGCCAAACATTATTACT ACGGTGGTAGCTATGCTATGGACTACTGGGGTCAAGGAACCT CAGTCACCGTCTCCTCA | 5 |
| FMC63VK | GACATCCAGATGACACAGACTACATCCTCCCTGTCTGCCTCTCT GGGAGACCGCGTCACCATCAGTTGCCGTGCAAGTCAGGACAT TAGTAAATACTTAAATTGGTATCAGCAGAAACCAGATGGAACT GTTAAACTCCTGATCTACCATACATCACGCTTACACTCAGGAGT CCCATCACGGTTCAGTGGCAGTGGGTCTGGAACAGATTATTCT CTCACCATTAGCAACCTGGAGCAAGAAGATATTGCCACTTACT TTTGCCAACAGGGTAATACGCTTCCGTACACGTTCGGAGGGG GGACTAAGTTGGAAATCAAA | 6 |

Figure 3:
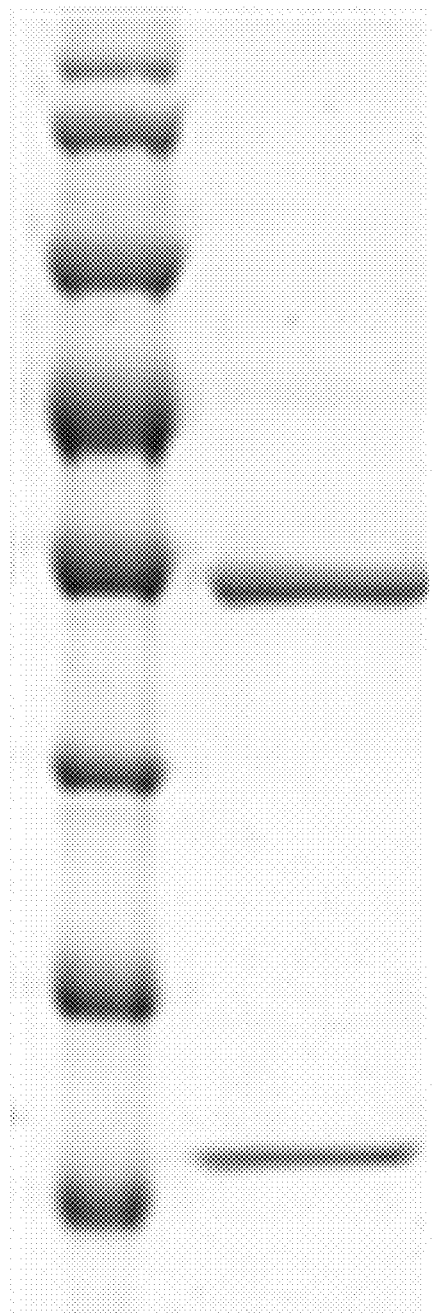
FIG. 3 shows the results of reducing SDS-PAGE (10%) analysis of the purified recombinant full-length FMC63 antibodies. M indicates protein molecular weight standards (170, 130, 100, 70, 55, 40, 35, 25, 15, 10 kD); FMC63 indicates purified recombinant murine monoclonal antibody FMC63. The heavy chain is about 50 kD, and the light chain is about 25 KD.

The synthesized polynucleotides encoding FMC63VH and the synthesized polynucleotides FMC63VK were cloned into two expression vectors: pMABG1 and pMABK, respectively. The plasmids expressing each of the purified heavy and light chains were co-transfected HEK293 cells. Recombinant FMC63 was expressed and obtained by using GE's Protein G affinity chromatography. Electrophoresis indicates that the purity of FMC63 is greater than 95% (FIG. 3).

Figure 4:
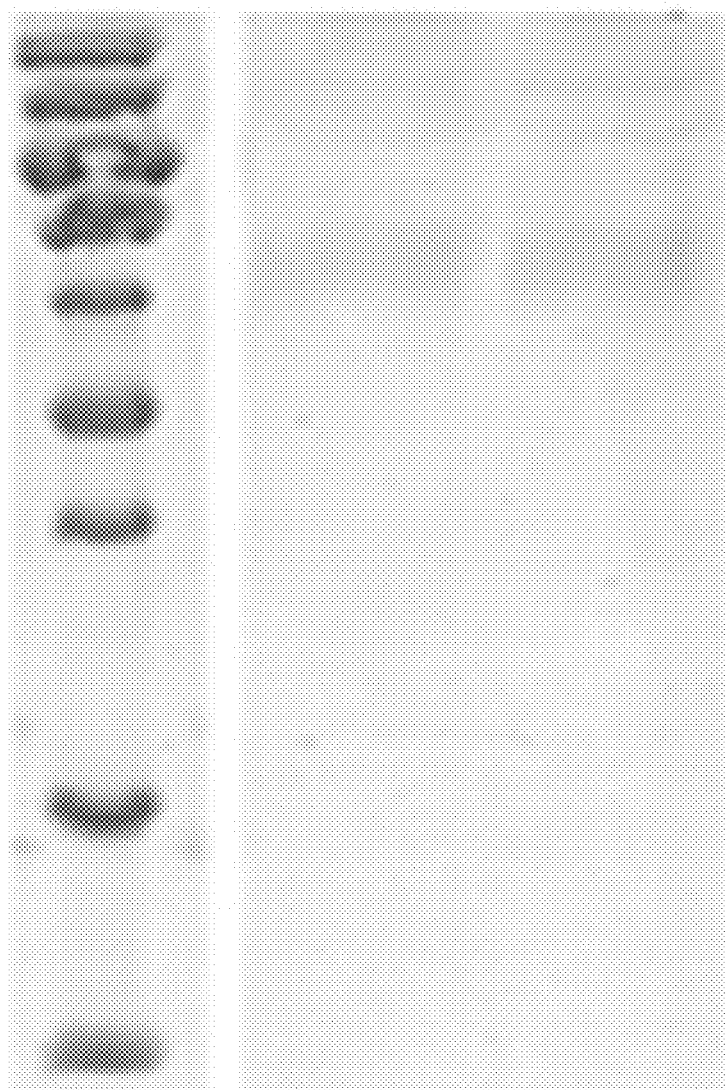
FIG. 4 shows the results of reducing SDS-PAGE (15%) analysis of purified recombinant CD19ECD-His fusion protein. M indicates protein molecular weight standards (170, 130, 100, 70, 55, 40, 35, 25, 15, 10 kD); "1" indicates purified recombinant CD19ECD-His; "2" indicates purified recombinant CD19ECD-His.

Recombinant human CD19 extracellular domain (CD19-ECD) were prepared. Polynucleotides encoding the CD19 extracellular domain was cloned into expression vector pTSE-His to construct recombinant CD19 antigen. The purified plasmids were transfected into HEK293 cells, and the expressed recombinant extracellular domain of CD19 (CD19-ECD-His) was purified using GE's Histrap FF affinity chromatography. SDS-PAGE shows a molecular weight of about 45-50 KD due to five glycosylation sites that CD19-ECD has and due to glycosylation heterogeneity when CD19-ECD was expressed in HEK293 cells (FIG. 4).

Figure 5:
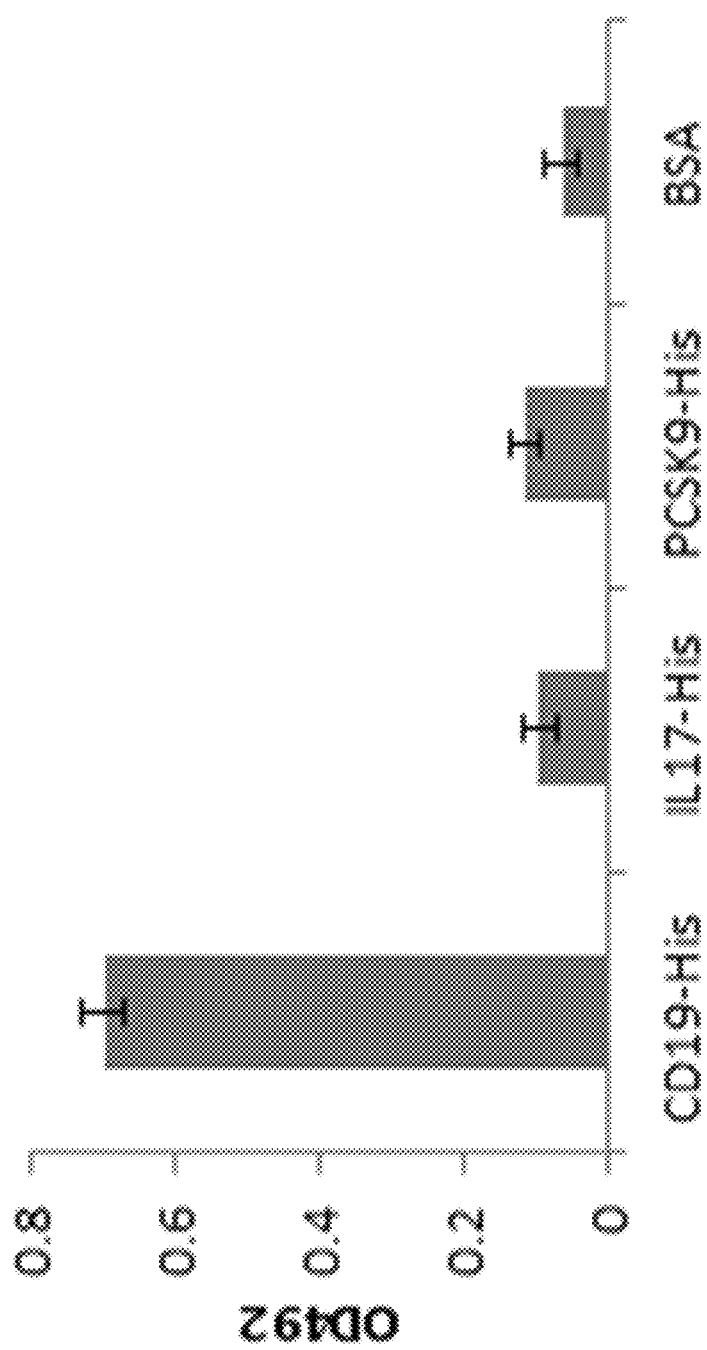
FIG. 5 illustrates results of ELISA analysis of recombinant murine antibody FMC63 in combination with different protein antigens. CD19-His: recombinant human CD19 extracellular domain with the His-tag fusion protein; IL17-His: recombinant human IL17 fusion protein with the His-tag; PCSK9-His: recombinant human PCSK9 with a His-tag fusion protein; BSA: bovine serum albumin protein.

Recombinant murine antibody FMC63 features were verified. The binding capacity of the recombinant FMC63 and recombinant human CD19 antigen was detected using ELISA. The results show that the recombinant murine antibody is capable of specifically binding to recombinant human CD19-ECD (FIG. 5).

Humanization of Heavy Chains of Murine Antibody FMC63

Humanized FMC63 heavy chain variable region was designed. First, the heavy chain complementarity-determining regions (HCDRs) and framework regions (FRs) of FMC63VH were determined. According to the definition of Kabat database, sequences of the HCDRs and FRs of FMC63VH are provided in Table 2.

TABLE 2

| Name | Sequence | SEQ ID NO: |
|---|---|---|
| FMC63VH | EVKLQESGPGLVAPSQSLSVTCTVSGVSLPD YGVSWIRQPPRKGLEWLGVIWGSETTYYNSA LKSRLTIIKDNSKSQVFLKMNSLQTDDTAIY YCAKHYYYGGSYAMDYWGQGTSVTVSS | 3 |
| HCDR1- Kabat | GVSLPDYGVS | 7 |
| HCDR2- Kabat | VIWGSETTYYNSALKS | 8 |
| HCDR3- Kabat | KHYYYGGSYAMDY | 9 |
| FR1- Kabat | EVKLQESGPGLVAPSQSLSVTCTVS | 10 |
| FR2- Kabat | WIRQPPRKGLEWLG | 11 |
| FR3- Kabat | RLTIIKDNSKSQVFLKMNSLQTDDTAIYYCA | 12 |
| FR3- Kabat | WGQGTSVTVSS | 13 |

According to IMGT database definitions, HCDRs and FRs of FMC63VH are provided in Table 3.

TABLE 3

| Name | Sequence | SEQ ID NO: |
|---|---|---|
| FMC63VH | EVKLQESGPGLVAPSQSLSVTCTVSGVSLPD YGVSWIRQPPRKGLEWLGVIWGSETTYYNSA LKSRLTIIKDNSKSQVFLKMNSLQTDDTAIY YCAKHYYYGGSYAMDYWGQGTSVTVSS | 3 |
| HCDR1- IMGT | GVSLPDYG | 14 |
| HCDR2- IMGT | IWGSETT | 15 |
| HCDR3- IMGT | KHYYYGGSYAMDY | 16 |
| FR1- IMGT | EVKLQESGPGLVAPSQSLSVICTVS | 17 |
| FR2- IMGT | VSWIRQPPRKGLEWLGV | 18 |
| FR3- IMGT | YYNSALKSRLTIIKDNSKSQVFLKMNSLQTD DTAIYYCA | 19 |
| FR3 | WGQGTSVTVSS | 20 |

Humanized templates were selected, and searches were performed using NCBI/IGBLAST tool to search for the highest homology to human antibody genes template IGHV4-59*05 based on FR1-CDR1-FR2-CDR2-FR3 sequence of FMC63VH. Searches were also performed using NCBI/IGBLAST tool to highest homology search of human antibody genes template IGHV3-48*03 based on FR1-FR2-FR3 sequence of FMC63VH. Searches were also performed using NCBI/IGBLAST tool to search for homology island's tallest man J region sequence IGHJ4*01 and IGHJ6*01 based on FR4 sequence of FMC63VH. Sequences of the templates are provided in Table 4.

TABLE 4

| Name | Sequence | SEQ ID NO: |
|---|---|---|
| U03893\|IGHV3-48*03 | EVQLVESGGGLVQPGGSLRLSCAAS GFTFSSYEMNWVRQAPGKGLEWVSY ISSSGSTIYYADSVKGRFTISRDNA KNSLYLQMNSLRAEDTAVYYCAR | 21 |
| M95118\|IGHV4-59*05 | QVQLQESGPGLVKPSETLSLTCTVS GGSISSYYWSWIRQPPGKGLEWIGR IYYSGSTYYNPSLKSRVTISVDTSK NQFSLKLSSVTAADTAVYYCA | 22 |
| J00256\|IGHJ6*01 | YYYYYGMDVWGQGTIVIVSS | 23 |
| J00256\|IGHJ4*01\| Homo sapiens\|F | YFDYWGQGTLVTVSS | 24 |

Humanized HCDRs of FMC63 were designed. Based CDR grafting strategy, various templates were selected, and three different humanized FMC63VH molecules were designed accordingly. Comparison between three different humanized FMC63VH is summarized in Table 5.

TABLE 5

| Polynucleotide Names | HCDR definitions | FR1-FR3 template | FR4 template | SEQ ID NO: |
|---|---|---|---|---|
| hFMC63VH | IMGT | IGHV4-59*05 | IGHJ4*01 | 25 |
| h1FMC63VH | Kabat | IGHV4-59*05 | IGHJ4*01 | 26 |
| h2FMC63VH | Kabat | IGHV3-48*03 | IGHJ4*01 | 27 |

With respect to hFMC63VH, the HCDRs of FMC63VH were transplanted to selected frame areas of IGHV4-59*05. The definition of HCDR is in accordance with the reference IMGT database, and IGHJ4*01 was select for FR4. The first version polynucleotides encoding the humanized heavy chain hFMC63VH was obtained accordingly (SEQ ID NO: Annex 4-1). With respect to h1FMC63VH, the HCDRs of FMC63VH were transplanted to select the frame area IGHV4-59*05. The definition of HCDR is in accordance with the reference Kabat database, and IGHJ4*01 was selected for FR4. The second version polynucleotides encoding humanized heavy chain h1FMC63VH was obtained accordingly (SEQ ID NO: Annex 4-2). With respect to h2FMC63VH, the HCDRs of FMC63VH were transplanted to choose IGHV3-48*03 framework regions. The definition of HCDR is in accordance with the reference Kabat HCDR database, and IGHJ6*01 was selected for FR4. The third version polynucleotides encoding the humanized FMC63VH polynucleotide h1FMC63VH was obtained accordingly (SEQ ID NO: Annex A-3)

Humanized FMC63VH were cloned and then expressed. Synthesized polynucleotides of three humanized heavy chain variable regions (hFMC63VH, h1FMC63VH, h2FMC63VH) are provided in Table 6.

vector (pTSEK-FMC63VK) was constructed to contain the murine-human chimeric light chain.

Figure 6:
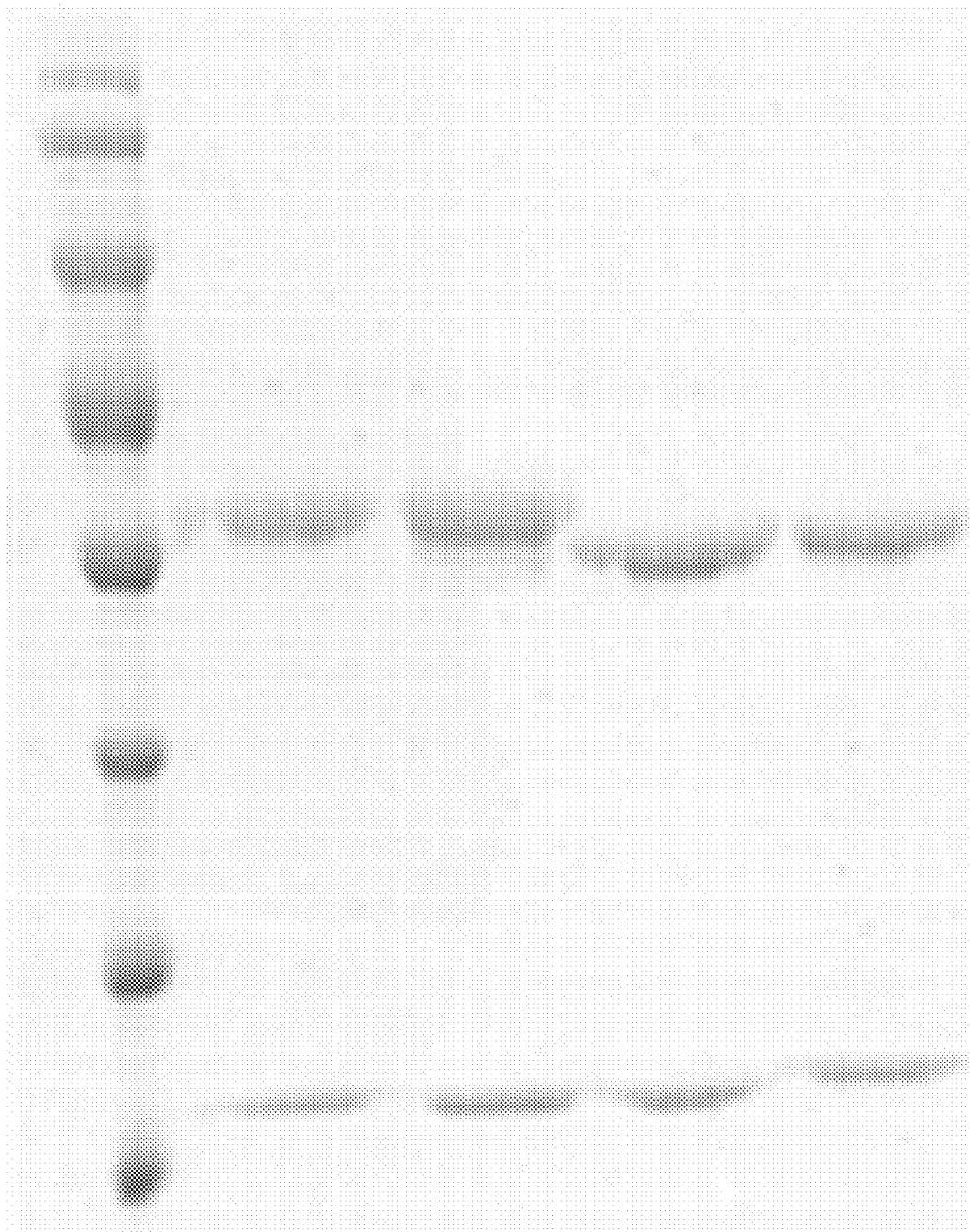
FIG. 6 shows the results of reducing SDS-PAGE (15%) analysis of the purified recombinant four kinds FMC63 full-length antibodies. M indicates protein molecular weight standards (170, 130, 100, 70, 55, 40, 35, 25, 15, 10 kD); "1" indicates purified recombinant chimeric FMC63; "2" indicates the purified recombinant hFMC63; "3" indicates purified recombinant h2FMC63. The heavy chain is about 50 KD, and the light chain is about 25 KD.
Figure 7:
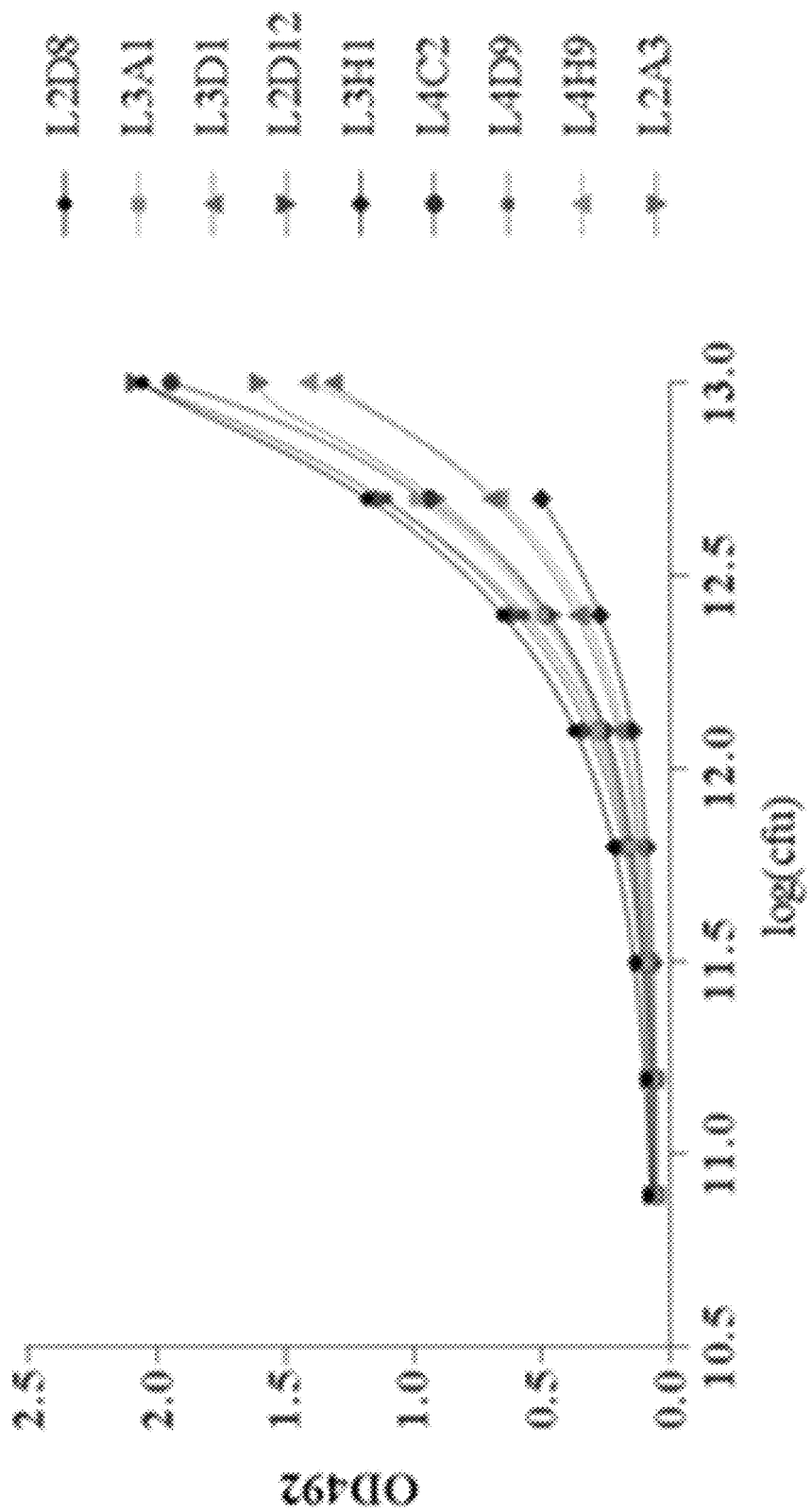
FIG. 7 illustrates a comparison between the relative affinities of different monoclonal antibodies measured using purified phage-Fab.
Figure 9:
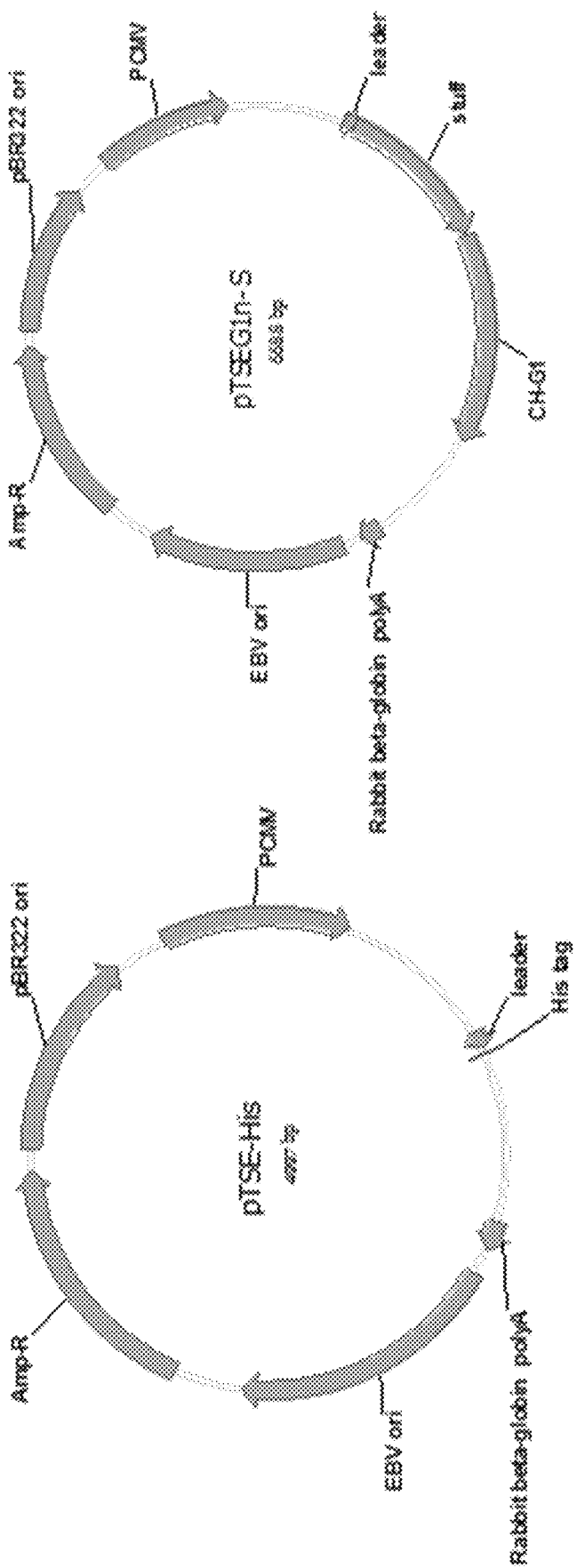
Figure 10:
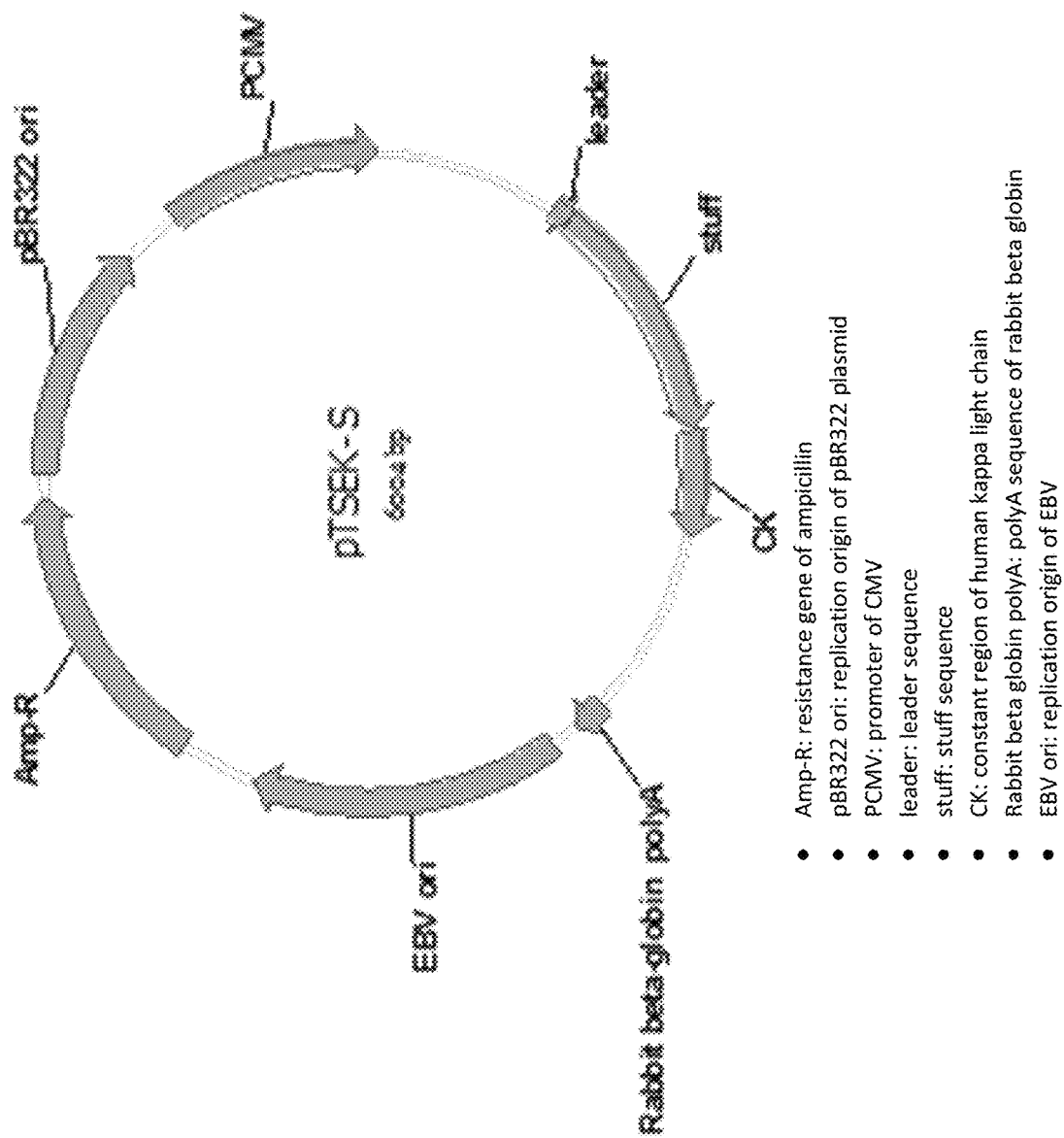

As illustrated in Table 7, the light and heavy chain expression vectors were co-transfected to HEK293 cells and were transiently expressed. After 3-4 days, supernatants were harvested. Four types of recombinant antibodies were purified using the use of Protein G affinity chromatography, and the purity thereof is more than 95% (FIG. 6).

The chimeric-FMC63 is a murine-human chimeric antibody (i.e., commonly referred to as the first generation of humanized antibody); wherein the variable regions are identical to antibodies of the murine donor while the constant region was replaced with human antibody constant region. Thus, the chimeric antibodies theoretically fully maintain biological activity of the antibodies of the murine donor. For the rest of humanized antibodies, various version of humanized heavy chains was adopted while the light chains are the same as the light chain of Chimeric FMC63 (See Table 7).

TABLE 6

| Polynucleotides | Sequences | SEQ ID NO: |
|---|---|---|
| hFMC63VH | CAGGTGCAACTGCAGGAGTCGGGCCCAGGACTGGTGAAGCC TTCGGAGACCCTGTCCCTCACCTGCACTGTCTCTGGGGTCTCA TTACCAGACTATGGTTGGAGCTGGATTCGGCAGCCGCCGGGG AAGGGACTGGAGTGGATTGGGCGTATCTGGGGTAGTGAAAC CACATACTACAACCCGTCCCTCAAGAGTCGCGTCACCATTTCC GTAGACACGTCCAAGAACCAGTTCTCCCTGAAGCTGAGCTCT GTGACCGCCGCAGACACGGCTGTGTATTACTGTGCGAAACAT TATTACTACGGTGGTAGCTATGCTATGGACTACTGGGGCCAA GGAACCCTGGTCACCGTCTCCTCA | 28 |
| h1FMC63VH | CAGGTGCAACTGCAGGAGTCGGGCCCAGGACTGGTGAAGCC TTCGGAGACCCTGTCCCTCACCTGCACTGTCTCTGGGGTCTCA TTACCAGACTATGGTGTGAGCTGGATTCGGCAGCCGCCGGGG AAGGGACTGGAGTGGATTGGGGTTATCTGGGGTAGTGAAAC CACATACTACAACAGCGCCCTCAAGAGTCGCGTCACCATTTCC GTAGACACGTCCAAGAACCAGTTCTCCCTGAAGCTGAGCTCT GTGACCGCCGCAGACACGGCTGTGTATTACTGTGCGAAACAT TATTACTACGGTGGTAGCTATGCTATGGACTACTGGGGCCAA GGAACCCTGGTCACCGTCTCCTCA | 29 |
| h2FMC63VH | GAGGTGCAGCTGGTGGAGTCTGGGGGAGGCTTGGTACAGCC TGGGGGGTCCCTGAGACTCTCCTGTGCAGCCTCTGGAGTGTC CCTGCCTGATTATGGCGTGTCCTGGGTCCGCCAGGCTCCAGG GAAGGGGCTGGAGTGGGTTTCAGTGATCTGGGGCAGCGAGA CAACCTACTACAACAGCGCCCTGAAGTCCCGATTCACCATCTC CAGAGACAATGCCAAGAACTCACTGTATCTGCAAATGAACAG CCTGAGAGCCGAGGACACGGCTGTGTATTACTGTGCGAAGCA CTACTACTACGGCGGCAGCTACGCTATGGACTACTGGGGCCA AGGAACCCTGGTCACCGTCTCCTCA | 30 |

Then these three humanized antibody heavy chain polynucleotides were expressed in vectors: pTSEG1n-S; named pTSEG1n-hFMC63VH, pTSEG1n-h1FMC63VH, and pTSEG1n-h2FMC63VH. The heavy chain gene encoding FMC63VH was also cloned into the expression vector pTSEG1n-S including the human antibody heavy chain gene. Accordingly, the expression vector (pTSEG1n-FMC63VH) was constructed to contain the murine-human chimeric heavy chain.

The light chain genes FMC63VK of the murine donor was cloned into the expression vector pTSEK-S containing the human antibody light chain. Accordingly, the expression

TABLE 7

| | Chimeric-FMC63 | hFMC63 | h1FMC63 | h2FMC63 |
|---|---|---|---|---|
| Heavy chain expression plasmid | pTSEG1n-FMC63VH | pTSEG1n-hFMC63VH | pTSEG1n-h1FMC63VH | pTSEG1n-h2FMC63VH |
| Light chain expression plasmid | pTSEK-FMC63VK | pTSEK-FMC63VK | pTSEK-FMC63VK | pTSEK-FMC63VK |

Activity comparison of heavy chains of the humanized antibody molecules was performed using Raji cells. Raji cell is a strain derived from human B lymphoma cell line. Raji cells were purchased from Chinese Academy of Medical Sciences, Institute of Basic Medical Cell Resource Center. The surface of Raji cells expresses antigen CD19, and the anti-CD19 antibody can be used to analyze the binding capacity of recombinant humanized monoclonal antibodies. By flow cytometry (IFA), binding abilities of the four recombinant humanized antibodies were analyzed. The binding analysis was performed between four humanized FMC63, and antigen CD19 expressed on Raji cell surfaces. The results show that the third version of a humanized antibody (h2FMC63) binds to the antigen expressed on the surface of Raji cells. Further, the binding ability of h2FMC63 reaches 82% of chimeric FMV63. This indicates that humanized heavy chain h2FMC63VH remains the binding ability to human CD19 antigen as compared with the binding ability of chimeric FMV63 (See Table 8).

TABLE 8

| Humanized antibody | MFI (GeoMean) | Relative affinity |
| --- | --- | --- |
| Chimeric-FMC(FMC) | 404 | 100% |
| hFMC | 67 | 17% |
| h1FMC | 186 | 46% |
| h2FMC | 330 | 82% |

Humanization of Light Chains of Murine Antibody FMC63

Humanized light chain of FMC63 was designed and generated by first building a light chain mutant library with storage capacity reaching 108. The human-derived light chain replacement library (Fab library) was built using a dual-carrier phage display system and the humanized heavy chain gene (h2FMC63VH). The correct rate for the light chain library is above 90%.

The light chain mutant library was screened, and various clones were identified. Recombinant CD19-His antigens were prepared. Using CD19-His antigens, the light chain mutant library was screened two rounds and enriched. More than 400 clones were identified using phage-ELISA, and more than 80% of these clones were positive. Among these clones, eight clones with the highest positive values were selected for further sequence analysis. The result shows that these 18 clones have different sequences. Among these 18 different clones, four clones were Lambda light chains, while the remaining 14 clones were kappa light chains.

The 18 clones were then prepared and purified to obtain phage-Fabs. After quantitation of the purified phage-Fabs, relative affinity analysis was performed on these phage-Fab using phage-ELISA. The result shows that three clones (L2D8, L2D12, L5F3, Specific sequences of Annex 6) have the highest affinity values (FIG. 5). Sequences of these three light chains are provided in Table 9. Further, a modification was made on L2D8 such that the mouse antibody light chain CDR region took the place of the corresponding portion of the L2D8, the new sequence to obtain L2D8-2 (SEQ ID: 37).

TABLE 9

| Name | Sequence | SEQ ID NO: |
| --- | --- | --- |
| L2D8 | DIQMTQSPSSLSASVGDRVTITCRASQSVGSFLAWYQQKPGKAPK LLIYGASSRESGVPSRFSGSGSGTDFTLTISSLQPEDFATYYCQQTYH NPETFGQGTKVEIK | 34 |
| L2D12 | SYELTQPPSVSVAPGQTARITCGGNDLRAQYVHWYQQKPGQAPV LVMYDDSKRPSGIPERFSGSNSGNTATLTISGTQAEDEADYYCQS WDRTSEPKVFGGGTKLTVL | 35 |
| L5F3 | SYELTQPPSVSVAPGQTARITCGGNNLGDNSARWYQQKPGQAPV LVIYGNSNRPSGIPERFSGSNSGNTATLTISGTQAEDEADYYCQVT DTRSTSVVFGGGTKLTVL | 36 |
| L2D8-2 | DIQMTQSPSSLSASVGDRVTITCRASQDISKYLNWYQQKPGKAPK LLIYHTSRLHSGVPSRFSGSGSGTDFTLTISSLQPEDFATYYCQQGN TLPYTFGQGTKVEIK | 37 |

Recombinant Humanized Murine Antibody FMC63

Three light chain gene (L2D8, L2D12, L5F3) were selected and cloned into light chain expression vectors. Using HEK293 transient expression system, three humanized monoclonal antibodies were obtained. Three kinds of people humanized antibody heavy chain gene are h2FMC63VH (pTSEG1n-h2FMC63VH).

Preliminary analysis of antibody activity was performed using cell lines expressing human CD19 CD19-K562 (3 #, 20141224) and flow cytometry (FCM). The results are illustrated in Table 10.

TABLE 10

| antibody Sample | FMC63VH + FMC63VK | h2FMC63VH + L5F3 | h2FMC63VH + L2D12 | h2FMC63VH + L2D8 |
| --- | --- | --- | --- | --- |
| MFI (Geo) | 47.2 | 147.3 | 55.5 | 125.3 |

The above data show that three new humanized antibody (L5F3, L2D12, L2D8) shows stronger binding abilities than murine antibody FMC63, wherein L5F3 and L2D8 shows significant improvement with respect to binding ability. Further, another

TABLE 11

| Name | Sequence | SEQ ID NO: |
|---|---|---|
| L2D8-2-DNA | GATATCCAGATGACCCAGAGCCCGAGCAGCCTGA GCGCGAGCGTGGGTGATCGCGTGACCATTACCTG Cagggcaagtcaggacattagtaaatatttaaat TGGTATCAGCAGAAACCGGGTAAAGCGCCGAAAC TGTTAATTTATcatacatcaagattacactcaGG CGTGCCGTCGCGTTTTAGCGGCTCGGGTTCGGGC ACCGATTTTACCCTGACCATCTCGAGCTTGCAGC CGGAGGACTTCGCCACCTACTATTGCaacaggg taatacgcttccgtacacgTTCGGTCAGGGCACC AAAGTGGAGATCAAA | 38 |

Cytotoxicity Comparison Between Two CARs

Lentiviral vectors that encode a CD19 CAR were generated, and the binding domain of the CD19 CAR was a humanized scFv against CD19 (SEQ ID: 43) of which the heavy chain (SEQ ID 27) and the light chain (SEQ ID: 37) were selected.

Figure 11:
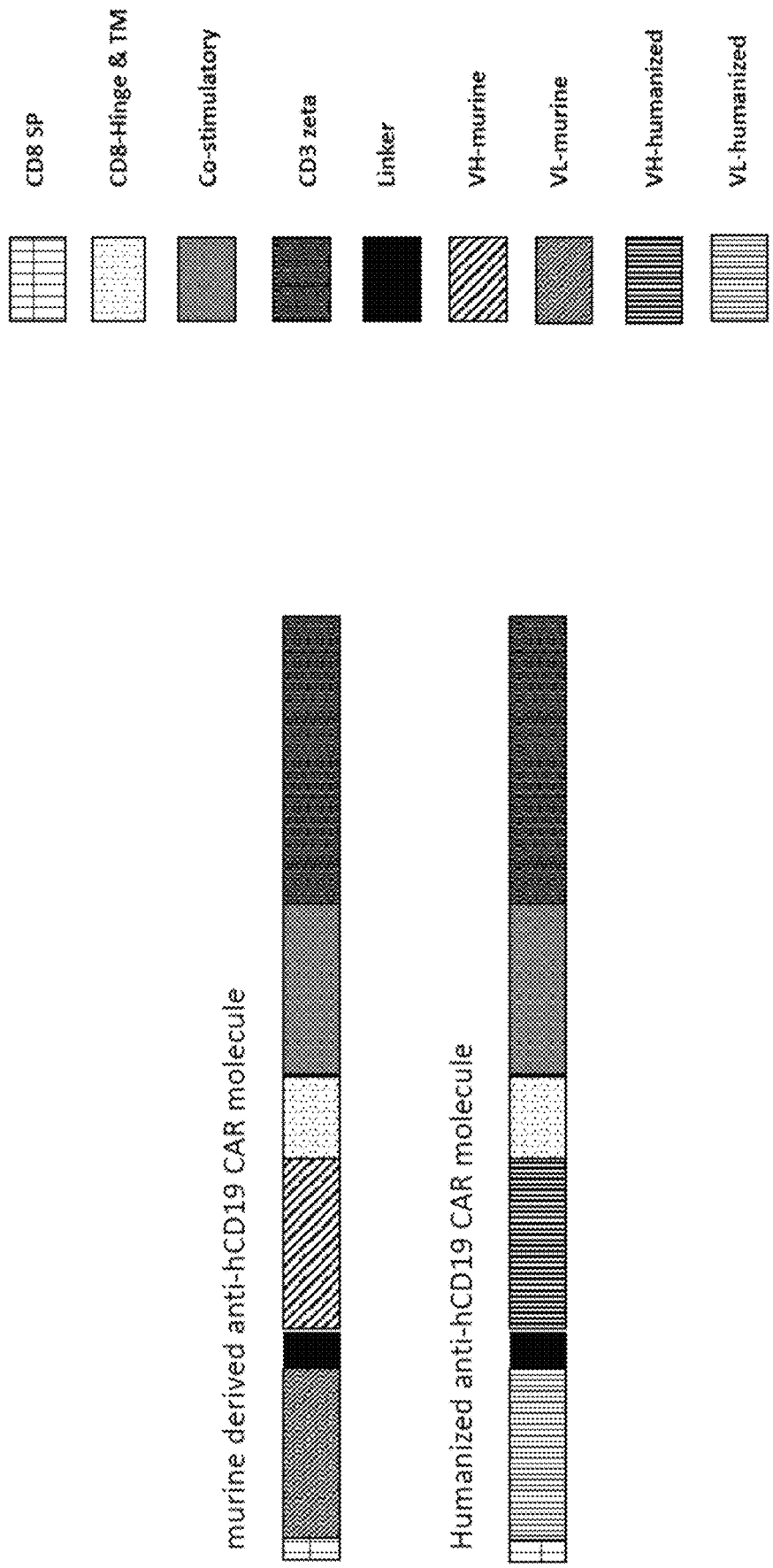
FIG. 11 is a schematic diagram illustrating molecular structures of two CARs.
Figure 12:
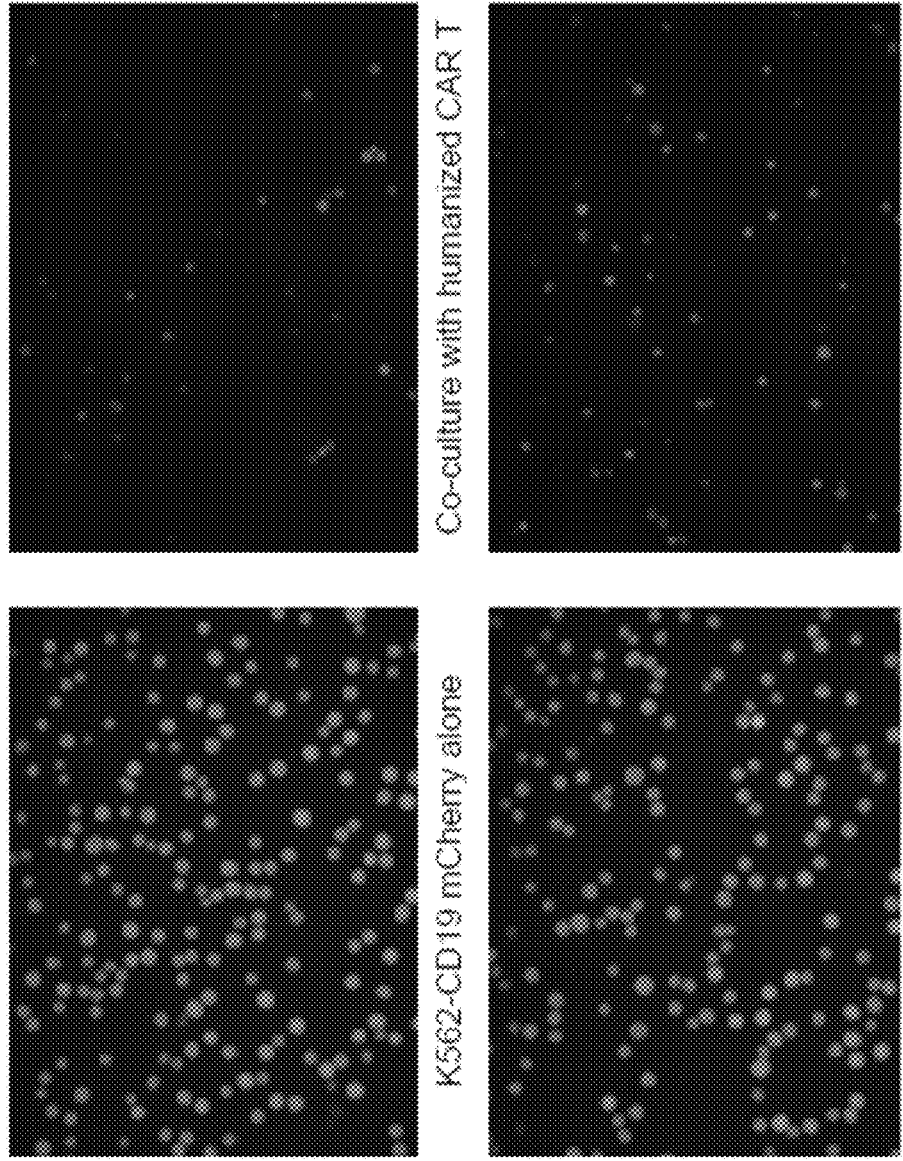
FIG. 12 show that T cells express two CARs provided in FIG. 11 killed CD19 positive cells when these T cells were co-cultured with CD19-positive cells.
Figure 13:
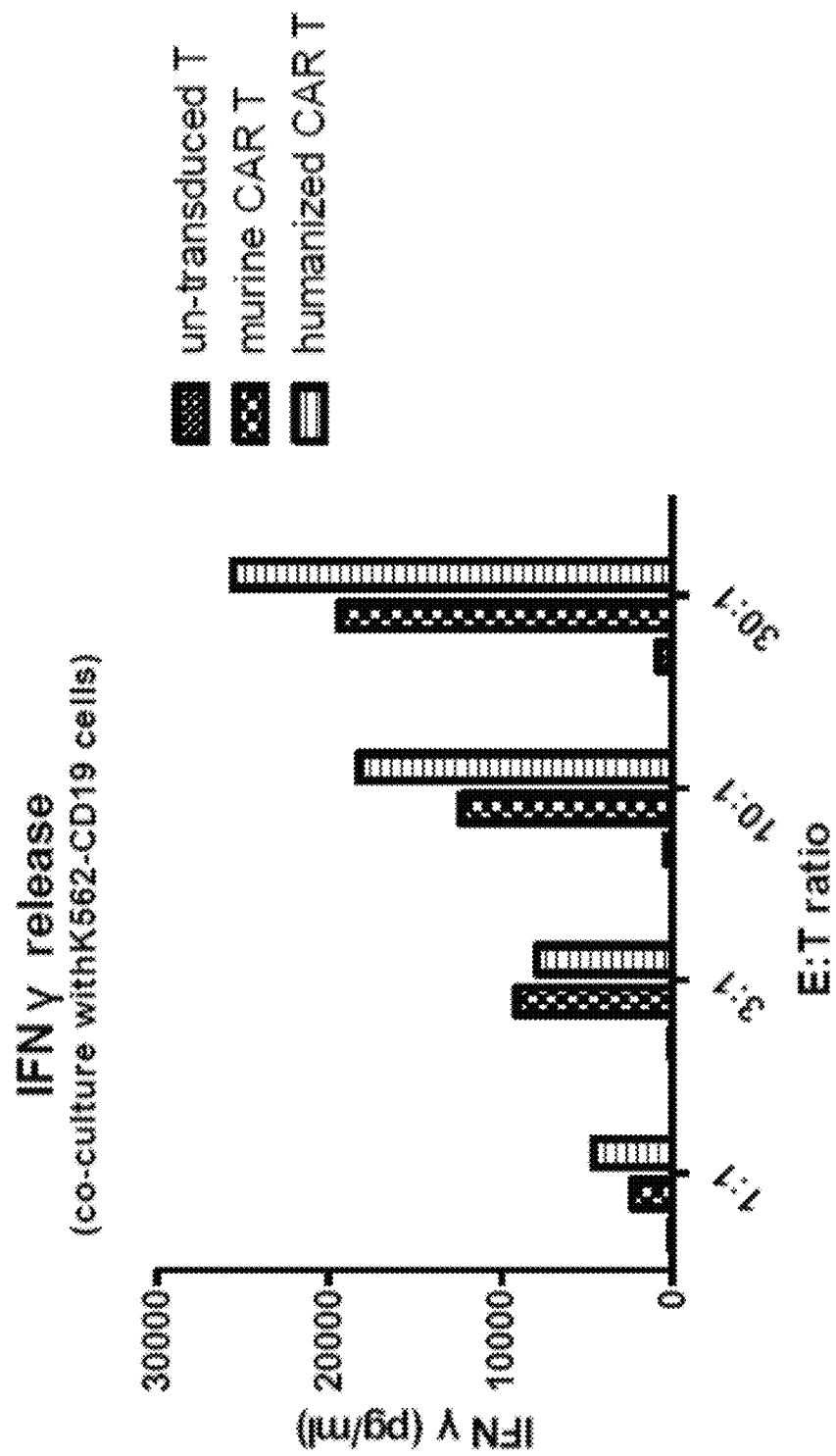
FIG. 13 illustrating comparison of amounts of IFN-gamma that are released from T cells expressing two CARs provided in FIG. 11, respectively.

Target cells (i.e., K562-CD19 mCherry) and various effector cells (i.e., T cells expressing CARs provided in FIG. 11 and Table 12) or negative control cells (i.e., non-transduced T cells) were cultured for about 24 hours with various ratios between the target cells and effector cells or negative control cells. Primary T cells were obtained from patients. The obtained primary T cells were transduced with lentiviral vectors to obtain modified T cells. Flow-cytometry was performed and analyzed to determine the expression of CARs in primary T cells. IFN-gamma production of transduced or non-transduced T cells was measured. As shown in FIGS. 12 and 13, IFN-gamma productions by T cells expressing humanized CAR was more than those with T cells expressing murine CAR and un-transduced CAR.

Techniques related to cell cultures, construction of cytotoxic T-lymphocyte assay may be found in Chimeric Receptors Containing CD137 Signal Transduction Domains Mediate Enhanced Survival of T Cells and Increased Antileukemic Efficacy In vivo Molecular Therapy vol. 17 no. 8, 1453-1464 August 2009, which is incorporated herein by reference.

TABLE 12

| SEQ ID NO: | Identity | Sequences |
|---|---|---|
| 39 | SP | MALPVTALLLPLALLLHAARP |
| 40 | Hinge & trans-membrane domain | AKPTTTPAPRPPTPAPTIASQPLSLRPEACRPAAGGAVHTRGLDFACDIYIW APLAGTCGVLLLSLVIT |
| 41 | Co-stimulatory region | KRGRKKLLYIFKQPFMRPVQTTQEEDGCSCRFPEEEEGGCEL |
| 42 | CD3-zeta | RVKFSRSADAPAYKQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR |
| 43 | scFV Humanized CD19 | DIQMTQSPSSLSASVGDRVTITCRASQDISKYLNWYQQKPGKAPKLLIYHTS RLHSGVPSRFSGSGSGTDFTLTISSLQPEDFATYYCQQGNTLPYTFGQGTKV EIKGGGGSGGGGSGGGGSEVQLVESGGGLVQPGGSLRLSCAASGVSLPDY GVSWVRQAPGKGLEWVSVIWGSETTYYNSALKSRFTISRDNAKNSLYLQ MNSLRAEDTAVYYCAKHYYYGGSYAMDYWGQGTLVTVSS |
| 44 | scFV CD19 | DIQMTQTTSSLSASLGDRVTISCRASQDISKYLNWYQQKPDGTVKLLIYHTS RLHSGVPSRFSGSGSGTDYSLTISNLEQEDIATYFCQQGNTLPYTFGGGTKL EITGGGGSGGGGSGGGGSEVKLQESGPGLVAPSQSLSVTCTVSGVSLPDY GVSWIRQPPRKGLEWLGVIWGSETTYYNSALKSRLTIIKDNSKSQVFLKMN SLQTDDTAIYYCAKHYYYGGSYAMDYWGQGTSVTVSS |
| 45 | CD3-zeta Wild | RVKFSRSADAPAYQQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR |

What is claimed is:

1. An isolated nucleic acid sequence encoding a humanized antibody or antigen binding fragment thereof, wherein the humanized antibody or antigen binding fragment thereof comprising a heavy chain variable (HCV) sequence having the amino acid sequence of SEQ ID NO: 27, and a light chain variable (LCV) sequence having the amino acid sequence of SEQ ID NO: 34, and wherein the humanized antibody or antigen binding fragment thereof binds CD19.

2. The isolated nucleic acid sequence of claim 1, wherein the antigen binding fragment is selected from the group consisting of a Fab, Fab', Fab'-SH, Fv, scFv, F(ab)2 and a diabody.

3. A vector comprising the isolated nucleic acid sequence of claim 1.

4. An isolated cell comprising the vector of claim 3.

5. The vector of claim 3, wherein the vector is an expression vector comprising control sequences operably linked to the isolated nucleic acid.

6. An isolated cell comprising the expression vector of claim 5.

7. A composition comprising a population of the cells of claim 4.

8. The composition of claim 7, wherein the cells comprise T cells.

9. The composition of claim 7, wherein the composition is a pharmaceutical composition.

10. A composition comprising a population of the cells of claim 6.

11. The composition of claim 10, wherein the cells comprise T cells.

12. The composition of claim 11, wherein the composition is a pharmaceutical composition.

13. A chimeric antigen receptor (CAR) comprising a scFv comprising a HCV sequence having the amino acid sequence of SEQ ID NO: 27 and a LCV sequence having the amino acid sequence of SEQ ID NO: 34, and wherein the CAR binds CD19.

14. The CAR of claim 13, wherein the CAR comprises an antigen binding domain comprising the scFv, a transmembrane domain, a costimulatory signaling region, and a CD3 zeta signaling domain.

15. The CAR of claim 14, wherein the CD3 zeta signaling domain comprises the amino acid sequence of SEQ ID NO: 42 or 45.

16. The CAR of claim 14, wherein the costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

* * * * *